United States Patent
Karino et al.

(12)

(10) Patent No.: US 9,295,455 B2
(45) Date of Patent: Mar. 29, 2016

(54) BIOPSY SYSTEM AND BIOPSY METHOD

(71) Applicant: Terumo Kabushiki Kaisha, Tokyo (JP)

(72) Inventors: Wataru Karino, Kanagawa (JP); Yuichi Tada, Kanagawa (JP)

(73) Assignee: TERUMO KABUSHIKI KAISHA, Shibuya-ku, Tokyo (JP)

( * ) Notice: Subject to any disclaimer, the term of this patent is extended or adjusted under 35 U.S.C. 154(b) by 195 days.

(21) Appl. No.: 13/866,065

(22) Filed: Apr. 19, 2013

(65) Prior Publication Data

US 2013/0281844 A1    Oct. 24, 2013

Related U.S. Application Data

(60) Provisional application No. 61/636,051, filed on Apr. 20, 2012.

(51) Int. Cl.
| | |
|---|---|
| *A61B 8/00* | (2006.01) |
| *A61B 10/04* | (2006.01) |
| *A61B 8/08* | (2006.01) |
| *A61B 8/12* | (2006.01) |
| *A61B 10/02* | (2006.01) |
| *A61B 17/34* | (2006.01) |

(52) U.S. Cl.
CPC ............... *A61B 10/04* (2013.01); *A61B 8/0841* (2013.01); *A61B 8/12* (2013.01); *A61B 8/445* (2013.01); *A61B 10/0283* (2013.01); *A61B 2017/3413* (2013.01)

(58) Field of Classification Search
CPC ............... A61B 10/0283; A61B 10/04; A61B 2017/3413; A61B 8/12; A61B 8/0841; A61B 8/445

See application file for complete search history.

(56) References Cited

U.S. PATENT DOCUMENTS

| | | | | |
|---|---|---|---|---|
| 2003/0093104 | A1* | 5/2003 | Bonner et al. | 606/185 |
| 2006/0184016 | A1* | 8/2006 | Glossop | 600/434 |
| 2008/0091104 | A1* | 4/2008 | Abraham | 600/439 |
| 2008/0097239 | A1* | 4/2008 | Chang et al. | 600/562 |
| 2012/0179032 | A1* | 7/2012 | Bromander et al. | 600/434 |
| 2012/0259220 | A1* | 10/2012 | Sheldon et al. | 600/439 |

FOREIGN PATENT DOCUMENTS

JP   2003-164455 A   6/2003

* cited by examiner

*Primary Examiner* — Jonathan Cwern

(74) *Attorney, Agent, or Firm* — Buchanan Ingersoll & Rooney PC

(57) ABSTRACT

A biopsy system includes a tomographic image pick-up device which is insertable into a living body to pick-up a tomographic image of a bioptic target part in the living body to be subjected to biopsy, a guide wire configured to puncture the bioptic target part in the condition where the tomographic image obtained by the tomographic image pick-up device is being observed; and a biopsy device which is inserted along the guide wire to the bioptic target part in the living body after withdrawal of the tomographic image pick-up device out of the living body and by which tissue of the bioptic target part is sampled. The guide wire remains in the living body in the state of puncturing the bioptic target part even after the withdrawal of the tomographic image pick-up device.

7 Claims, 13 Drawing Sheets

BIOPSY SYSTEM AND BIOPSY METHOD

CROSS REFERENCES TO RELATED APPLICATIONS

This application is based on and claims priority to U.S. Provisional Application No. 61/636,051 filed on Apr. 20, 2012, the entire content of which is incorporated herein by reference.

TECHNICAL FIELD

The present disclosure generally relates to a biopsy system by which a biopsy device is inserted into a living body and tissue in the living body is sampled, for the purpose of biopsy, and a biopsy method in which the biopsy system is used.

BACKGROUND DISCUSSION

In conventional diagnosis of lung cancer, images of a patient's lungs are first picked up using X-rays or CT (computed tomography), and primary diagnosis is conducted. Based on the images picked up, the presence or absence of a nodule in the lung field is checked. When the presence of a nodule is confirmed, secondary diagnosis is conducted by a method in which a biopsy device is inserted into the bronchus through a bronchoscopy and tissue in the living body is sampled by the biopsy device. Then, vital histological diagnosis is conducted in which the sampled tissue is observed.

A conventional biopsy system for performing the above-mentioned biopsy is disclosed, for example, in Japanese Patent Laid-open No. 2003-164455. This application publication describes a technology using a system including an ultrasonic probe which acquires an ultrasonic image of the inside of a living body, and a puncture needle which protrudes from the ultrasonic probe and by which tissue is sampled.

In the technology described in Japanese Patent Laid-open No. 2003-164455, the ultrasonic probe is first inserted into the living body, and an image of the bioptic target part to be bioptically examined is acquired. Then, while observing the image picked up by the ultrasonic probe, the puncture needle is made to puncture the bioptic target part, thereby sampling the tissue.

According to the technology disclosed in Japanese Patent Laid-open No. 2003-164455, however, the ultrasonic probe constituting a tomographic image pick-up device and the puncture needle as a biopsy device are inserted into the living body in the mutually overlaid state. In addition, the biopsy device is thick, in order to sample the tissue in an amount sufficient for biopsy. As a result, in the technology disclosed in the above-mentioned application publication, the member inserted into the living body together with the ultrasonic probe is large in diameter. This leads to a problem, for example, in that the biopsy device and the ultrasonic probe cannot be inserted into a peripheral region where the nodule is found of the bronchus in the vicinity of the alveoli.

In addition, when the biopsy device to be inserted together with the ultrasonic probe constituting the tomographic image pick-up device is reduced in diameter, the amount of the tissue which can be sampled would be decreased.

Furthermore, there has also been proposed a biopsy method as follows. First, only an ultrasonic probe is inserted into a living body to confirm the position of the bioptic target part, followed by pulling the ultrasonic probe out of the living body. Thereafter, a biopsy device is inserted to the position where the bioptic target part is confirmed by the ultrasonic probe, and tissue is sampled. According to this biopsy method, the biopsy device can be inserted to a peripheral region in a living body.

However, the ultrasonic probe has been withdrawn out of the living body when the tissue is sampled by inserting the biopsy device. This has led to the problem that it cannot be checked whether the biopsy device has assuredly reached the bioptic target part.

SUMMARY

The biopsy system and biopsy method disclosed here allows a biopsy device to be rather assuredly inserted to a bioptic target part located in a peripheral region in a living body and a large amount of tissue can be sampled.

According to one aspect, a biopsy system for performing biopsy of a bioptic target part in a living body comprises: an ultrasonic probe positionable in and removable from the living body and comprised of a main body section and a sensor section configured to transmit signals which are reflected off the bioptic target part in the living body and receive the reflected signals to produce a tomographic image of the bioptic target part; a guide wire possessing a distal end configured, while observing the tomographic image of the bioptic target part, to puncture the bioptic target part so that the guide wire is in a punctured state, with the main body section of the ultrasonic probe including a guide wire insertion hole having open opposite ends for receiving the guide wire, and the ultrasonic probe being movable along the guide wire when the guide wire is positioned in the guide wire insertion hole; and a biopsy device movable along the guide wire while the guide wire is in the punctured state and after the ultrasonic probe is removed from the living body to guide movement of the biopsy device to the bioptic target part, the biopsy device being configured to contact the bioptic target part and obtain a tissue sample of the bioptic target part for biopsy.

According to another aspect, a biopsy system comprises: a tomographic image pick-up device insertable into a living body and configured to pick-up signals used to generate a tomographic image of a bioptic target part in the living body to be subjected to biopsy; a guide wire configured to puncture the bioptic target part while observing the tomographic image obtained by the tomographic image pick-up device; a biopsy device insertable along the guide wire to the bioptic target part in the living body after withdrawing the tomographic image pick-up device from the living body and configured to obtain a tissue sample of the bioptic target part for the biopsy; and the guide wire remaining in the living body in a punctured state in which the guide wire is puncturing the bioptic target part even after withdrawing the tomographic image pick-up device from the living body.

The biopsy device is preferably inserted after the withdrawal of the tomographic image pick-up device out of the living body. Therefore, the biopsy device can be inserted to a peripheral region in the living body. Furthermore, marking is conducted by causing the guide wire to puncture the bioptic target part while observing the tomographic image picked up by the tomographic image pick-up device. The biopsy device is inserted along the guide wire which remains in the punctured state relative to the bioptic target part. Therefore, the biopsy device can be relatively assuredly inserted to the bioptic target part located in a peripheral region in the living body.

Since only the biopsy device is inserted into the living body, the thickness of the biopsy device can be set without any significant restriction imposed by the size (diametric size) of other devices. Therefore, the thickness of the biopsy device can be enlarged to such a level that the biopsy device can be inserted to the peripheral region of the living body. This makes it also possible to increase the amount of tissue which can be sampled by the biopsy device.

According to another aspect, a biopsy method involves: inserting a probe into a living body bioptic target part in the living body bioptic target part in the living body; puncturing a bioptic target part in the living body with a guide wire while observing a tomographic image of the bioptic target part produced based on signals emitted from the probe toward the bioptic target part and signals reflected from the bioptic target part and received by the probe; withdrawing the probe while the bioptic target part remains punctured by the guide wire; inserting a biopsy device along the guide wire and guiding movement of the biopsy device by moving the biopsy device along the guide wire while the bioptic target part remains punctured by the guide wire; and sampling tissue of the bioptic target part through use of the biopsy device.

The biopsy system and biopsy method permit a biopsy device to be rather assuredly inserted to a bioptic target part located in a peripheral region in a living body, for example, in the vicinity of the alveoli in the bronchus, and also allow a relatively large amount of tissue to be sampled.

BRIEF DESCRIPTION OF THE DRAWINGS

FIGS. 20A and 20B illustrate another modification of the tomographic image pick-up device used in the biopsy system disclosed here, wherein FIG. 20A is a cross-sectional view showing the condition where a first sensor is inserted in a main body section, and FIG. 20B is a cross-sectional view showing the condition where a second sensor is inserted in the main body section.

FIGS. 21A and 21B illustrate a further modification of the tomographic image pick-up device used in the biopsy system, wherein FIG. 21A is a cross-sectional view, and FIG. 21B is a front view.

DETAILED DESCRIPTION

Figure 1:
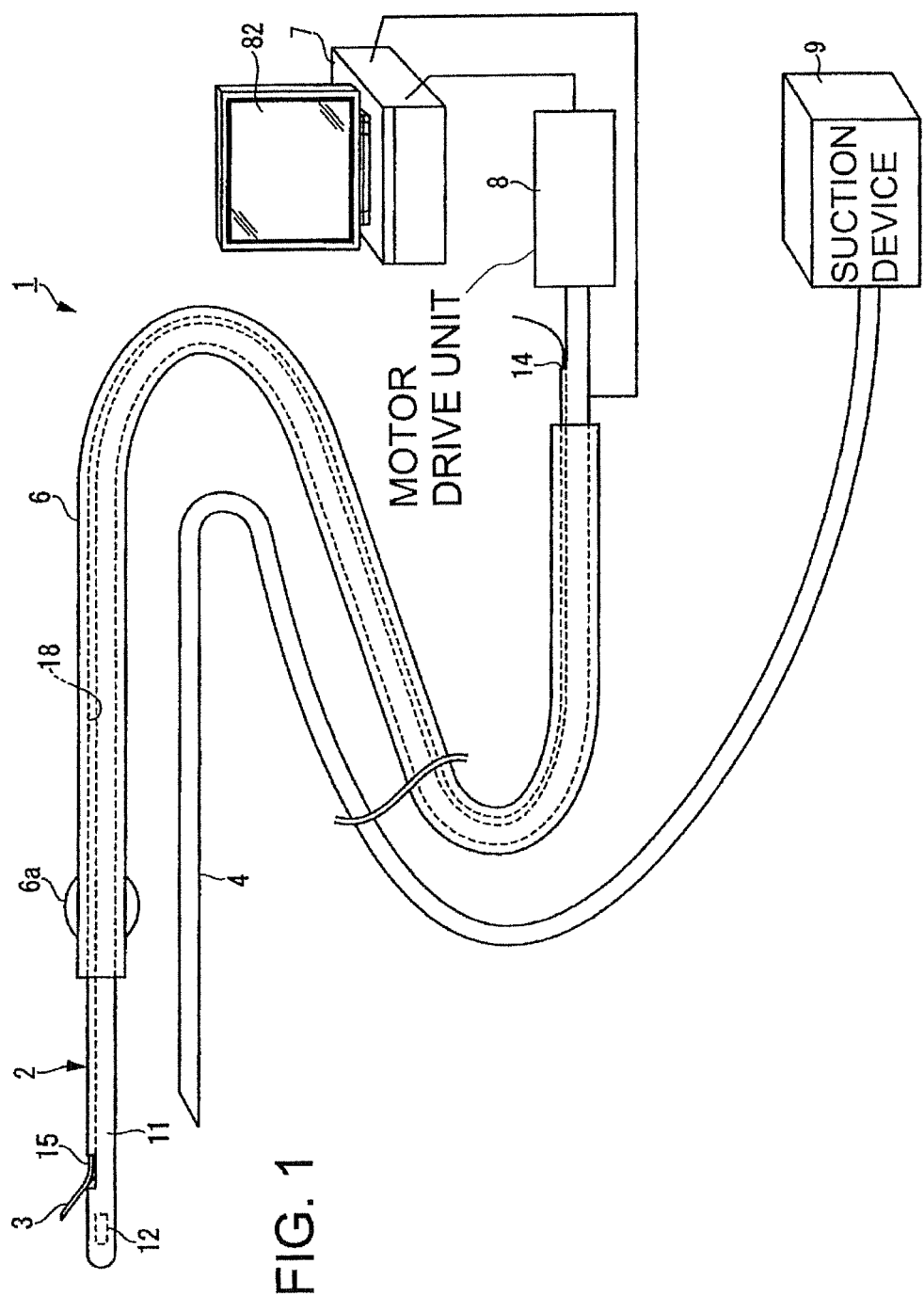
FIG. 1 is a schematic illustration of a first embodiment of a biopsy system representing one example of the disclosure here.

Embodiments of the biopsy system according to the present disclosure will now be described below, referring to FIGS. 1 to 19. Similar features are identified in the drawings by common reference numerals Example of Configuration of Biopsy System An example of a configuration of the biopsy system according to a first embodiment (hereinafter referred to as "this embodiment") will now be described with reference to FIGS. 1 to 4.

The biopsy system 1 shown in FIG. 1 is a system by which tissue in a living body, specifically, tissue of a bioptic target part (nodule) in a bronchus in this embodiment, is sampled by suction. The biopsy system 1 includes an ultrasonic probe 2, a guide wire 3, a biopsy device 4, and a guide sheath 6 in which the ultrasonic probe 2 and the biopsy device 4 are inserted and passed.

In addition, the biopsy system 1 has an image diagnosis unit 7 and a motor drive unit 8 which are connected to the ultrasonic probe 2, and a suction device 9 connected to the biopsy device 4. The ultrasonic probe 2, the image diagnosis unit 7, and the motor drive unit 8 constitute a tomographic image pick-up device. The image diagnosis unit 7 is provided with an image display unit 82 on which an in vivo tomographic image picked up by the ultrasonic probe 2 is displayed.

Ultrasonic Probe

Figure 2:
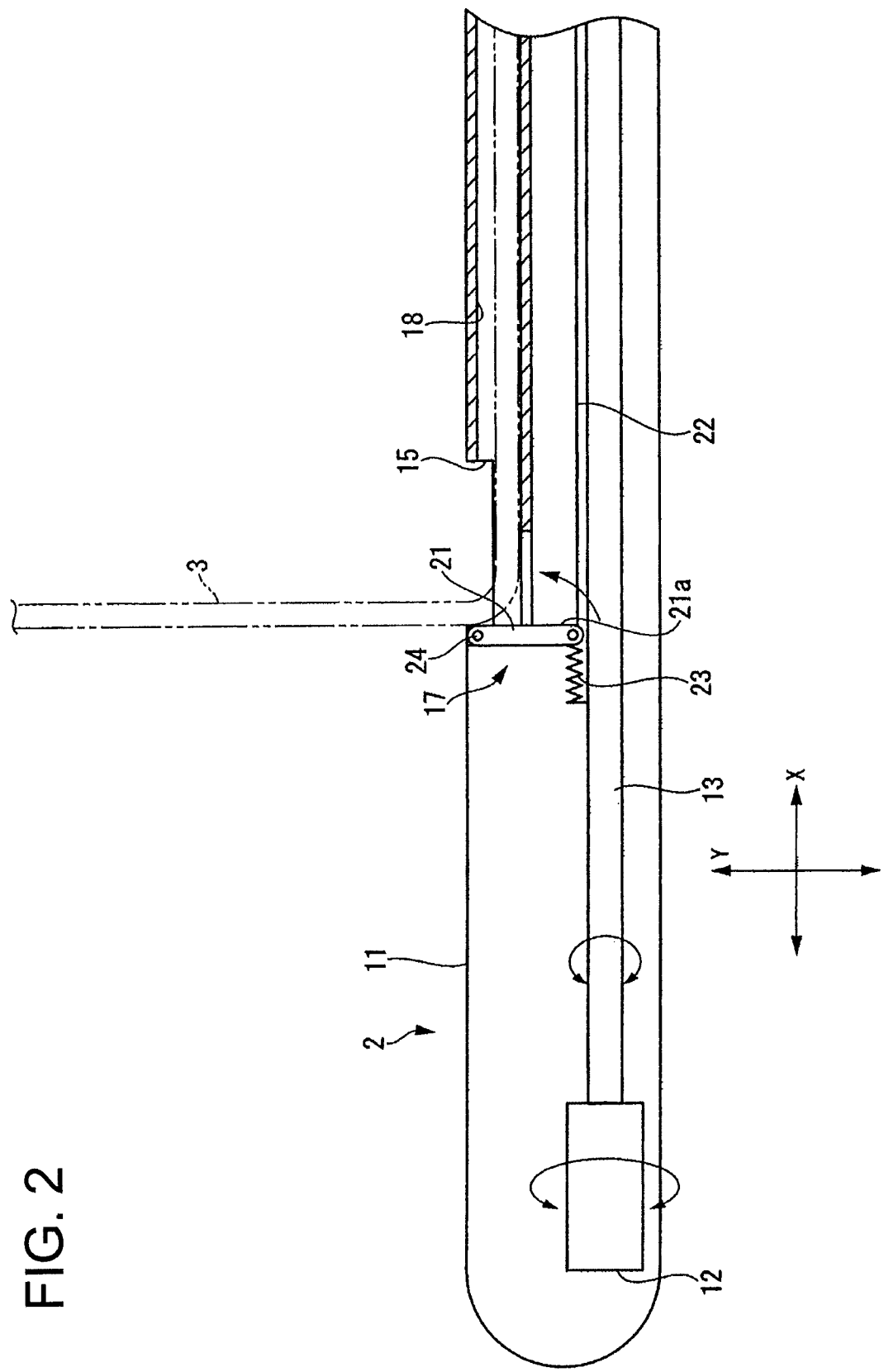
FIG. 2 is a cross-sectional view of a part of a tomographic image pick-up device in the biopsy system disclosed here.

The ultrasonic probe 2 includes a main body section 11 possessing a tubular shape, a sensor section 12 incorporated in the main body section 11, and a drive shaft 13 (see FIG. 2). To the ultrasonic probe 2, the guide wire 3 for applying a treatment to a living body is attached in such a manner that it can be advanced and retracted.

The main body section 11 is formed in an elongated roughly cylindrical shape, with both ends closed. The shape of the main body section 11 is not restricted to the roughly cylindrical shape, and various other shapes are possible, for example pyramidal shapes or shapes which are elliptic in cross-section orthogonal to the axial direction of the main body section. A distal portion in the axial direction, or a portion on the side of insertion into a living body, of the main body section 11 is formed in a roughly hemispherical shape for facilitating insertion into a lumen of a living body. In addition, the main body section 11 is flexible so that it can be bent according to bends of the body lumen.

The main body section 11 includes an insertion port 14 on the proximal end side. The main body section 11 includes a protrusion port 15 on the distal end side. The insertion port 14 and the protrusion port 15 communicate with each other through an insertion hole 18. The guide wire 3 is inserted into the main body section 11 via the insertion port 14. The guide wire 3 inserted via the insertion port 14 is inserted and extends along the insertion hole 18. A distal portion of the guide wire 3 inserted into and extending along the insertion hole 18 (guide wire insertion hole) protrudes through the protrusion port 15 to the outside of the main body section 11.

The following description refers to the axial direction of the main body section 11 as a first direction X, and refers to the direction in the plane formed by the first direction X and the protruding direction of the guide wire 3 which is orthogonal to the first direction X as a second direction Y.

As shown in FIG. 2, the main body section 11 is provided with a protrusion angle control mechanism 17 adapted to control the protrusion angle θ of the guide wire 3. The protrusion angle control mechanism 17 includes a control piece 21, an operating wire 22, a biasing member 23, and a control drive section.

The control piece 21, by making contact with the guide wire 3, bends a distal portion of the guide wire 3 to thereby control the protrusion angle at which the guide wire 3 protrudes from the protrusion port 15. The control piece 21 is tongue-like in shape (tongue-shaped), and is disposed at the protrusion port 15 on the side of the distal end of the main body section 11. A pivot 24 is attached to one end, on the protrusion port 15 side, of the control piece 21. In addition, the control piece 21 is turnably supported on the main body section 11 through the pivot 24. The control piece 21 is turned along the plane defined by the first direction X and the second direction Y.

In addition, the guide wire 3 makes contact with a contact surface 21a, on the side opposite to the distal portion of the main body section 11, of the control piece 21. In an initial state shown in FIG. 2, the contact surface 21a of the control piece 21 is erect along the second direction Y, and is orthogonal to the direction (the first direction X) in which the opening of the protrusion port 15 and the insertion hole 18 extend.

The biasing member 23 is attached to the other end of the control piece 21 opposite to the one end at which the pivot 24 is located. The biasing member 23 is composed of a helical extension spring. The biasing member 23 is fixed to the other end of the control piece 21, and biases the other end of the control piece 21 toward the distal end side of the main body section 11.

The operating wire 22 is attached to the other end of the control piece 21. The operating wire 22 is so provided that it can be advanced and retracted (moved in the distal and proximal directions) along the first direction X in which the main body section 11 extends. An end portion of the operating wire 22 on the side opposite to the control piece 21 is connected to the control drive section.

Figure 8:
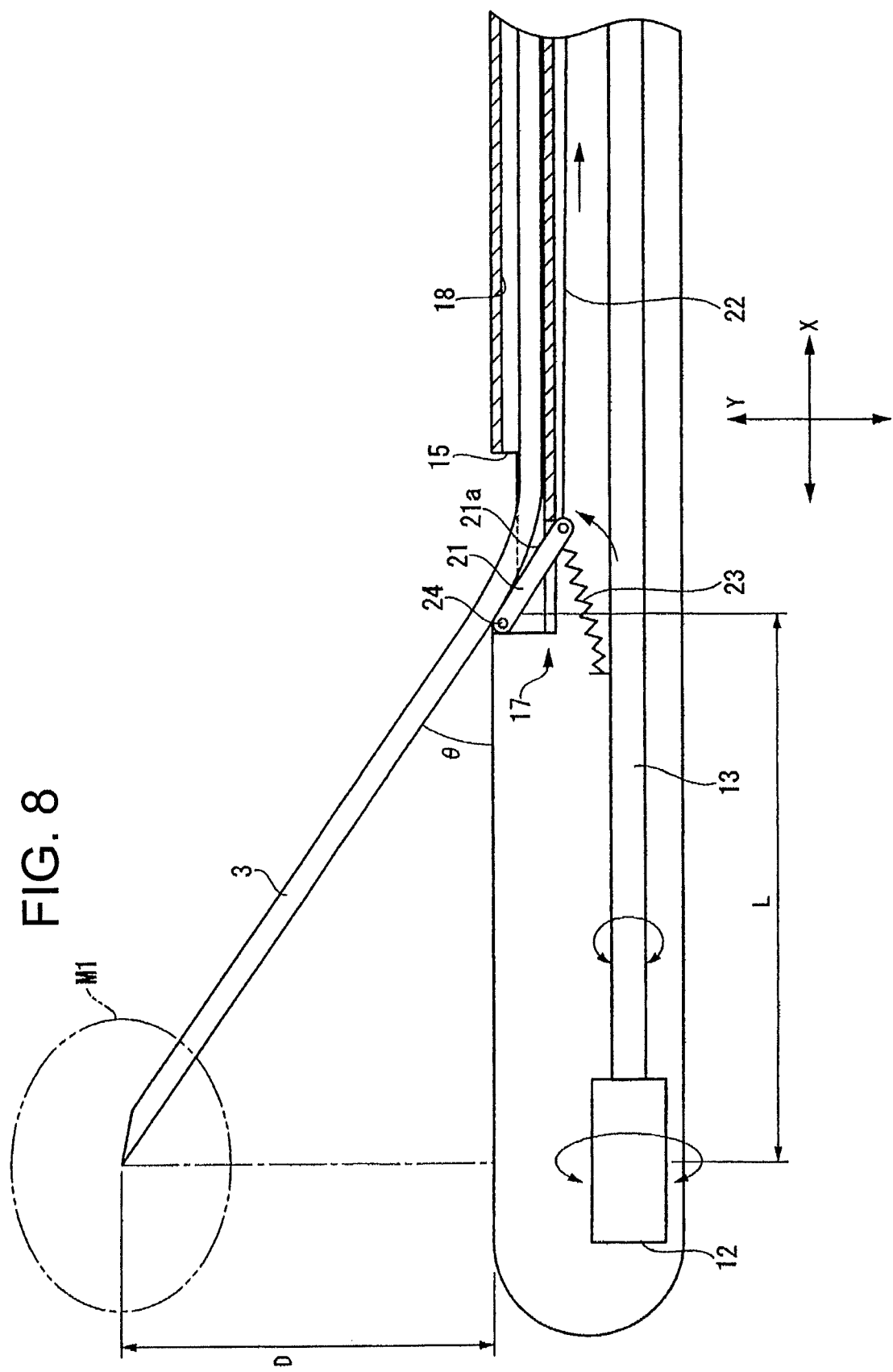
FIG. 8 is an illustration of a state in use of the first embodiment of the biopsy system disclosed here, showing the condition where the guide wire has punctured a nodule.

When the control drive section is driven to operate (pull) the operating wire 22 toward the proximal end side in the axial direction (proximal direction) of the main body section 11, the control piece 21 is turned in such a direction that the other end of the control piece 21 approaches the protrusion port 15, against the biasing force of the biasing member 23 (see FIG. 8). In other words, the control piece 21 is inclined relative to the first direction X.

In addition, when the driving of the control drive section is stopped so as to relax the pull on the operating wire 22, the control piece 21 is turned by the biasing force of the biasing member 23 in such a direction that the other end of the control piece 21 is moved away from the protrusion port 15. Thus, by operating the control piece 21 so that the control piece turns, the angle at which the guide wire 3 protrudes from the protrusion port 15 (hereinafter referred to as "the protrusion angle") is controlled.

While an example in which the control piece 21 of the protrusion angle control mechanism 17 possesses a tongue-like shape has been described in this embodiment, this is not restrictive. For example, the control piece 21 may possess a tubular shape through which the guide wire 3 passes. In the case where the control piece 21 is formed in a tubular shape, the control piece 21 is preferably so disposed that the tube hole of the control piece 21 communicates with the opening of the protrusion port 15.

The sensor section 12 for transmitting signals and receiving reflected signals (signals reflected off living body tissue) is rotatably provided at a distal portion of the main body section 11. The sensor section 12 is disposed on the distal end side of the main body section 11 in relation to the protrusion port 15 provided in the main body section 11. The sensor section 12 is provided at a position which is deviated or spaced in the second direction Y to be farther from the protrusion port 15 than the axis of the main body section 11. The position at which to provide the sensor section 12 is not restricted to a position deviated from the axis. For instance, the sensor section 12 may be disposed on the axis of the main body section 11. Thus, the position at which the sensor section 12 is located is not specifically restricted.

The sensor section 12 includes a roughly cylindrical ultrasonic transducer which transmits an ultrasonic wave to a living body, and a reception element which receives a reflected ultrasonic signal, that is, the ultrasonic wave reflected from the living body. Thus, the ultrasonic probe 2 in this embodiment is a device for acquiring an in vivo tomographic image as an ultrasonic image. The drive shaft 13 is attached to the sensor section 12.

The drive shaft 13 is positioned in and extends along the main body section 11, ranging from a distal portion to a proximal portion of the main body section 11. The drive shaft 13 is connected to the motor drive unit 8 (see FIG. 3) located at a proximal portion in the axial direction of the main body section 11. The driving operation of the motor drive unit 8 produces a rotating force transmitted through the drive shaft 13 to the sensor section 12. The sensor section 12 is thus rotated, with the first direction X as the center of rotation. This helps ensure that the ultrasonic probe 2 in this embodiment has a scanning range of 360 degrees around a side surface portion of the main body section 11, or in directions orthogonal to the first direction X.

While an example in which the ultrasonic image is acquired over a 360 degree range by rotating the sensor section 12 has been described in this embodiment, the invention is not limited in this way. For example, the sensor section 12 may not necessarily be rotated. A plurality of ultrasonic transducers may be arranged in an arcuate pattern. The ultrasonic image may be acquired in a range of equal to or less than 360 degrees. In other words, in the present invention, it suffices that a tomographic image of the inside of a living body inclusive of a bioptic target part M1 can be acquired.

Control System of Tomographic Image Pick-up Device

The control system of the tomographic image pick-up device configured as above will now be described with reference to FIG. 3.

Figure 3:
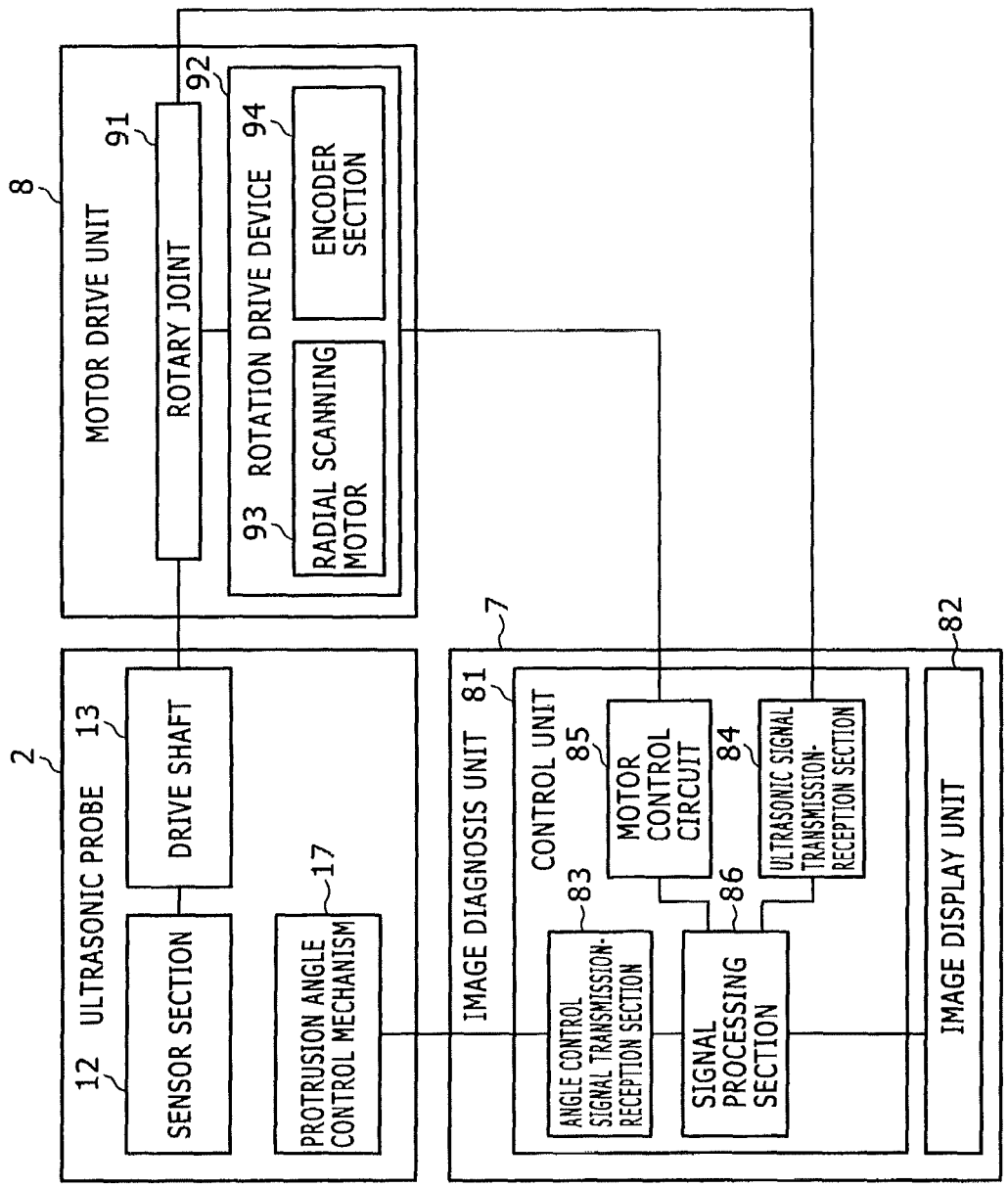
FIG. 3 is a block diagram showing a control system in the tomographic image pick-up device in the biopsy system disclosed here.

As shown in FIG. 3, the image diagnosis unit 7 includes a control unit 81 and an image display unit 82. The control unit 81 includes an angle control signal transmission-reception section 83, an ultrasonic signal transmission-reception section 84, a motor control circuit 85, and a signal processing section 86.

The angle control signal transmission-reception section 83 is connected to the protrusion angle control mechanism 17 in the ultrasonic probe 2. In addition, the angle control signal transmission-reception section 83 is connected to the signal processing section 86. The angle control signal transmission-reception section 83 receives an angle control signal computed by the signal processing section 86. The angle control signal transmission-reception section 83 transmits the received angle control signal to the protrusion angle control mechanism 17. Based on the angle control signal received, the protrusion angle control mechanism 17 drives the control drive section so as to control the angle of the control piece 21 (see FIG. 2).

Furthermore, the angle control signal transmission-reception section 83 receives angle information on the control piece 21 (see FIG. 2) from the protrusion angle control mechanism 17, and transmits it to the signal processing section 86.

The ultrasonic signal transmission-reception section 84 is connected to the sensor section 12 of the ultrasonic probe 2 and to the signal processing section 86. The ultrasonic signal transmission-reception section 84 is connected to the sensor section 12 by way of a rotary joint 91 and through the drive shaft 13. The ultrasonic signal transmission-reception section 84 receives an ultrasonic oscillation signal from the signal processing section 86, and transmits the received ultrasonic oscillation signal to the sensor section 12. Then, the sensor section 12 oscillates the ultrasonic transducer, based on the ultrasonic oscillation signal sent from the ultrasonic signal transmission-reception section 84.

In addition, to the ultrasonic signal transmission-reception section 84, the reflected ultrasonic signal received by the reception element of the sensor section 12 is sent from the sensor section 12. Then, the ultrasonic signal transmission-reception section 84 transmits the received reflected ultrasonic signal to the signal processing section 86. The signal processing section 86 is connected to the image display unit 82.

The signal processing section 86 is connected to the motor drive unit 8 through the motor control circuit 85. The motor drive unit 8 includes the rotary joint 91 and a rotation drive device 92.

To the rotation drive device 92, the drive shaft 13 of the ultrasonic probe 2 is connected through the rotary joint 91. The rotation drive device 92 includes a radial scanning motor 93 and an encoder section 94.

The radial scanning motor 93 is driven to rotate, based on a rotation signal sent from the signal processing section 86 through the motor control circuit 85. Then, a rotating force of the radial scanning motor 93 is transmitted through the rotary joint 91 to the drive shaft 13 and the sensor section 12 of the ultrasonic probe 2. In addition, rotational information on the radial scanning motor 93 is detected by the encoder section 94. The encoder section 94 transmits the detected rotational information on the radial scanning motor 93 to the signal processing section 86 through the motor control circuit 85.

The signal processing section 86 produces an ultrasonic tomographic image, based on the reflected ultrasonic signal which is received by the sensor section 12 and the rotational information on the radial scanning motor 93 which is received from the encoder section 94. Then, the ultrasonic tomographic image produced by the signal processing section 86 is displayed on the image display unit 82.

While an example in which an ultrasonic probe having an ultrasonic transducer, or so-called ultrasonic endoscope, is applied as the probe of the tomographic image pick-up device has been described in this embodiment, this is not restrictive. For instance, an Optical Coherence Tomography (OCT) system which has a sensor section composed of a light irradiation element for irradiating a living body with light and a light reception element for receiving the light reflected from the living body and which uses optical interference may be applied as the tomographic image pick-up device. Thus, it suffices for the tomographic image pick-up device to be a device by which an in vivo tomographic image can be acquired.

Guide Wire

The guide wire 3 is in the shape of an elongated thin wire. A distal portion of the guide wire 3 protruding from the protrusion port 15 of the ultrasonic probe 2 is configured to be able to puncture a living body (in this embodiment, a bronchus N1 and a bioptic target part M1). Specifically, the distal portion has a tapered-off shape. In other words, the distal end of the guide wire 3 is sharpened so that it can puncture a living body. As the material forming the guide wire 3, or so-called blank material, there can be used various metallic materials such as stainless steels (e.g., all kinds of SUS, such as SUS304, SUS 303, SUS316, SUS316L, SUS316J1, SUS316J1L, SUS405, SUS430, SUS434, SUS444, SUS429, SUS430F, and SUS302), piano wire, cobalt alloys, and pseudo-elastic alloys. Preferred among these are stainless steels and cobalt alloys, and more preferred are stainless steels. The guide wire 3 is configured to have an overall length, from the distal end of the guide wire to the proximal end of the guide wire, of 500 to 2,000 mm and an outside diameter of 0.3 to 1.0 mm. In addition, the outer circumference of the guide wire 3 is preferably coated with PTFE or silicone, for reducing the sliding resistance generated between the guide wire 3 and the ultrasonic probe 2. The guide wire 3 is used to guide the biopsy device 4 to the bioptic target part M1. In addition, it suffices for the guide wire 3 to be visually checkable on a tomographic image, and, therefore, the guide wire 3 can be formed to be extremely thin.

Biopsy Device

The biopsy device 4 will now be described below, referring to FIGS. 1 and 4.

Figure 4:
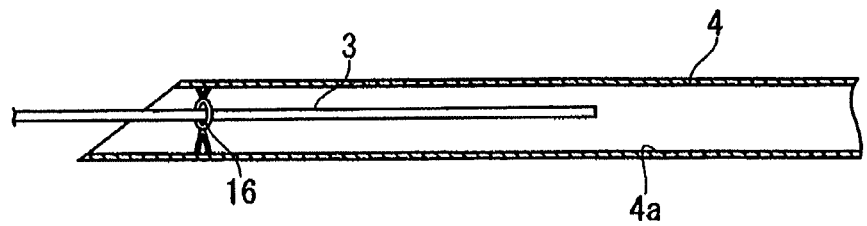
FIG. 4 is a cross-sectional view showing a biopsy device and a guide wire according to the first embodiment of the biopsy system disclosed here.

As shown in FIGS. 1 and 4, the biopsy device 4 possesses a hollow tubular shape open at both ends. As shown in FIG. 4, a ring section 16 through which to pass the guide wire 3 is provided in a tube hole 4a of the biopsy device 4. With the guide wire 3 passed through the ring section 16, the biopsy device 4 is supported on the guide wire 3 so that it can be advanced and retracted.

As shown in FIG. 1, a distal portion in the axial direction of the biopsy device 4 is so formed as to be able to puncture a living body, so that tissue of the living body can be sampled. In addition, the suction device 9 is provided at a proximal portion in the axial direction of the biopsy device 4. When suction is applied to the inside of the tube hole 4a (see FIG. 4) of the biopsy device 4 by the suction device 9, the tissue sampled by the distal portion of the biopsy device 4 is sucked or drawn-in.

Guide Sheath

The ultrasonic probe 2 and the biopsy device 4 as above-described are inserted into or positioned in the guide sheath 6 (see FIG. 1). The guide sheath 6 is formed in a tubular shape open at both ends, and is flexible. The guide sheath 6 guides the ultrasonic probe 2 and the biopsy device 4 to a central portion of a bronchus N1, and supports the insertion of the ultrasonic probe 2 and the biopsy device 4.

A balloon 6a configured to stretch and contract, and to be inflated and deflated, is provided at a distal portion in the axial direction of the guide sheath 6. When the balloon 6a is inflated in the condition where the guide sheath 6 is positioned in the bronchus N1, the balloon 6a makes secure contact with the inner wall surface of the bronchus N1 (see FIG. 6).

While an example in which the balloon 6a is provided on the guide sheath 6 has been described in this embodiment, the balloon is not limited in this regard. The balloon 6a may be provided on a distal portion of the ultrasonic probe 2. Thus, it suffices for the balloon 6a to be provided on at least one of the ultrasonic probe 2 and the guide sheath 6. Furthermore, the balloon 6a may be disposed at that part of the ultrasonic probe 2 at which the sensor section 12 is provided.

In addition, while an example in which the biopsy system 1 is provided with the guide sheath 6 has been described in this embodiment, it is also possible to implement the biopsy system without the guide sheath 6.

Biopsy Method

A biopsy method in which the biopsy system 1 configured as above is used will now be described below with reference to FIGS. 1 to 11.

Figure 5:
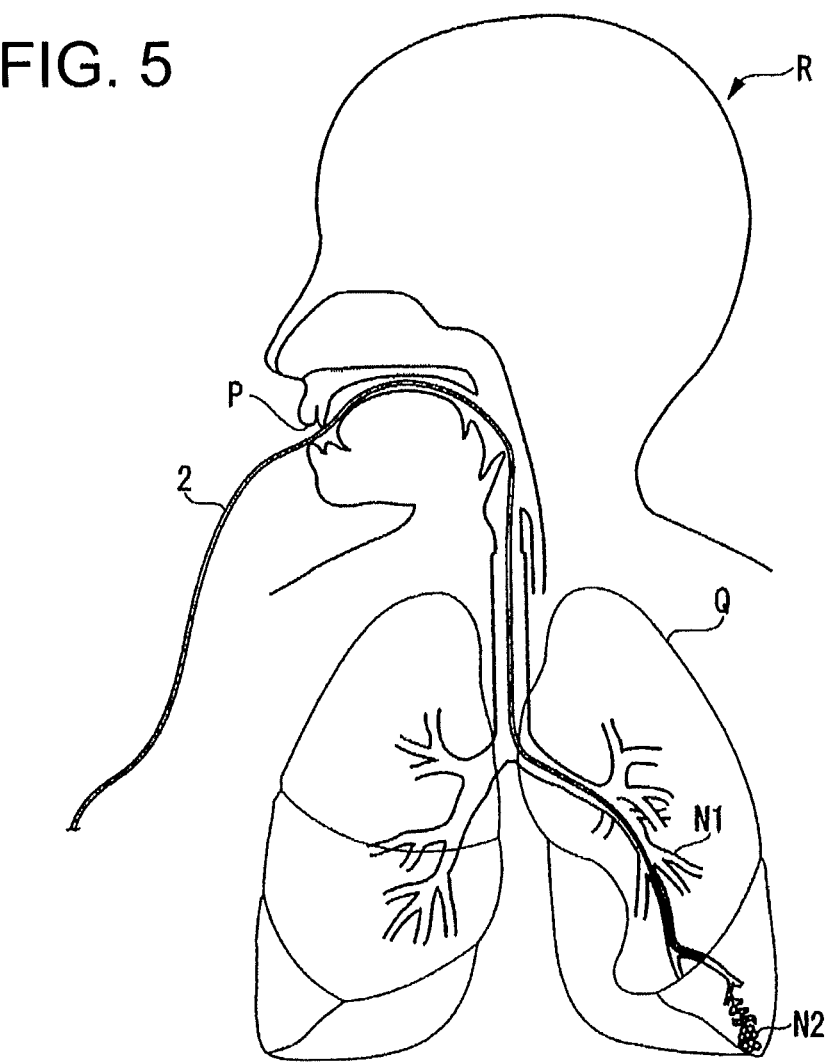
FIG. 5 is an illustration of a state in which the biopsy system is inserted into a living body.
Figure 6:
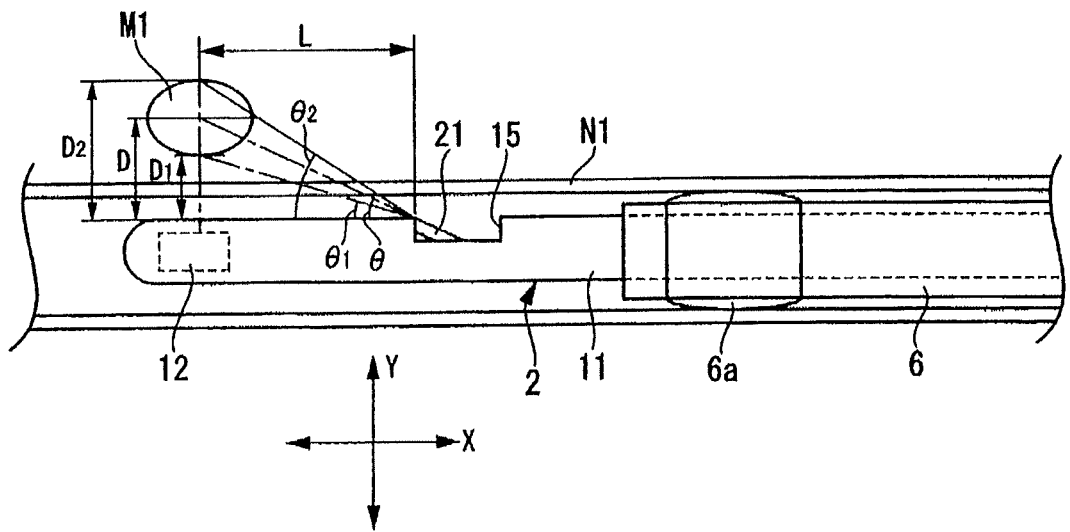
FIG. 6 is an illustration of a state in use of the first embodiment of the biopsy system disclosed here, showing the condition where the tomographic image pick-up device is inserted in a bronchus.
Figure 7:
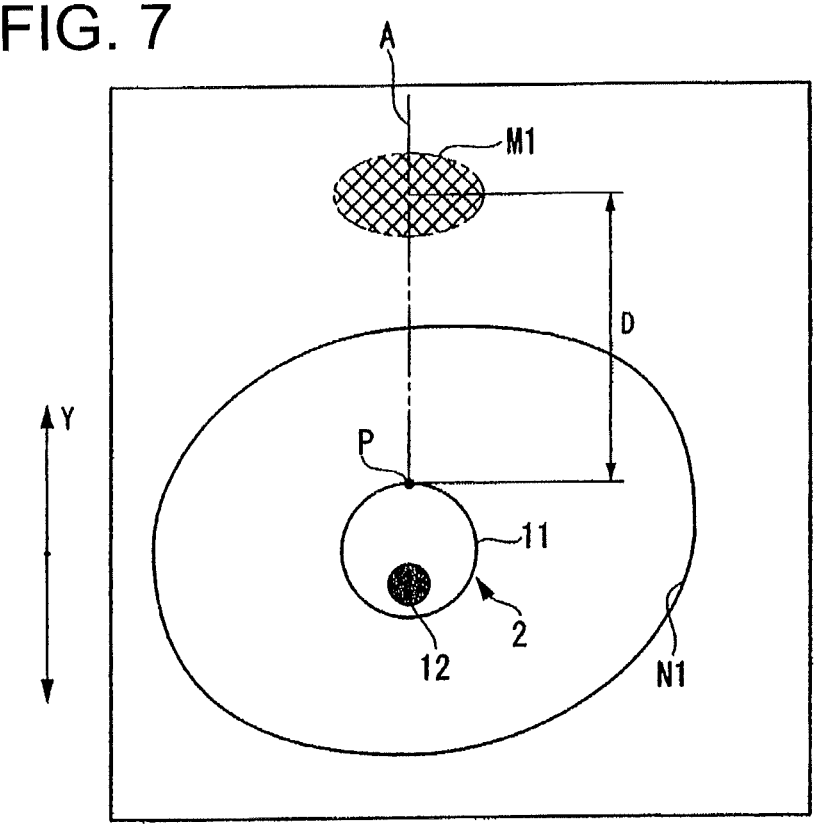
FIG. 7 illustrates an example of an in vivo tomographic image displayed on an image diagnosis unit in the first embodiment of the biopsy system disclosed here, where the tomographic image shows the condition where the bioptic target part is confirmed by the tomographic image pick-up device.

FIG. 5 illustrates a state in which the ultrasonic probe 2 is inserted in a living body, with the guide sheath 6 omitted, FIG. 6 shows a state in which a distal portion of the ultrasonic probe 2 is positioned in the vicinity of a bioptic target part, FIG. 7 shows an example of a tomographic image displayed on the image display unit 82 of the image diagnosis unit 7, and FIG. 8 shows a state in which the guide wire 3 has punctured a bioptic target part.

First, as shown in FIG. 5, the ultrasonic probe 2 is inserted into a bronchus N1 of a lung Q through an oral cavity P of a patient R. In this instance, the ultrasonic probe 2 is positioned in and extends along the tube hole of the guide sheath 6 as shown in FIG. 1. Next, as shown in FIG. 6, the balloon 6a at the distal end of the guide sheath 6 is inflated so that the balloon 6a securely contacts the inner wall surface of the bronchus N1. As a result, the periphery of the bronchus N1 beyond the balloon 6a is occluded. Subsequently, a liquid serving as an ultrasound transmitting medium is injected into the occluded part of the bronchus N1 which is on the peripheral side relative to the balloon 6a. Examples of the liquid to be injected include physiological saline.

With the peripheral side of the bronchus N1 thus filled with the liquid, an air layer that would otherwise hamper the propagation of ultrasound can be removed.

Next, the ultrasonic probe 2 is inserted to the bioptic target part M1, or the part where a so-called nodule is found. The aspect of the method described above involves inserting or positioning the ultrasonic probe 2 in the vicinity of the bioptic target part M1 after the injection of the liquid, but the method is not limited in this regard. The injection of the liquid may be conducted after the ultrasonic probe 2 is inserted into or positioned at the vicinity of the bioptic target part M1.

Before inserting of the ultrasonic probe 2 into the bronchus N1 (living body), the sensor section 12 is preliminarily driven to thereby display an ultrasonic image (tomographic image) on the image display unit 82 of the image diagnosis unit 7. Then, an ultrasonic image (tomographic image) of the inside of the bronchus N1 is acquired by the ultrasonic probe 2. Subsequently, the position of the ultrasonic probe 2 is adjusted so that the bioptic target part M1 is captured on the ultrasonic image obtained by the ultrasonic probe 2.

The driving of the sensor section 12 of the ultrasonic probe 2 may be conducted after the insertion into the bronchus N1.

Here, the sensor section 12 is disposed at a position deviated in the second direction Y from the axis of the main body section 11, namely, at a position opposite to the side of the protrusion port 15 in the second direction Y. This helps ensure that in the main body section 11 which is roughly circular in cross-section, the position of the protrusion port 15 from which the guide wire 3 protrudes can be rather easily determined. Then, the operator rotates the ultrasonic probe 2 so that the protrusion port 15 is directed toward the bioptic target part M1 side in the second direction Y.

In addition, a mark P indicative of the side on which the protrusion port 15 of the main body section 11 is provided, namely, indicative of the position where the guide wire 3 protrudes, may be displayed on the image display unit 82. In this case, even if the sensor section 12 is provided on the axis of the main body section 11, the position of the protrusion port 15 can be rather easily determined.

Next, the operator designates the bioptic target part M1 (the part to be bioptically examined) on the ultrasonic image displayed, and inputs positional information on the bioptic target part M1 to the image diagnosis unit 7 (see FIG. 3). Based on the positional information thus inputted, the control unit 81 of the image diagnosis unit 7 measures the distance D from the outer wall of a side surface portion of the main body section 11 to a central portion of the bioptic target part M1 along the second direction Y.

The aspect of the method described above involves the operator designating the bioptic target part M1. But it is also possible to use a method in which the control unit 81 automatically searches the bioptic target part M1 from the ultrasonic image and measures the distance D. In addition, in the case where the bioptic target part M1 is not located in the plane A (see FIG. 7) formed by the first direction X and the protruding direction of the guide wire 3 when the bioptic target part M1 is designated, the control unit 81 may provide a display on the image display unit 82 indicating that it is necessary to rotate the ultrasonic probe 2.

As shown in FIG. 6, the distance L from the sensor section 12 to the protrusion port 15 where the guide wire 3 protrudes, along the first direction X, is always constant. Information on the distance L is preset in the control unit 81.

Then, the control unit 81 computes, based on the distance D and the distance L, the protrusion angle θ, at which the guide wire 3 protrudes from the probe 2. The protrusion angle θ can be computed, for example, from the following formula 1:

$$\tan \theta = D/L \qquad \text{Formula 1}$$

Subsequently, the control unit 81 produces an angle control signal on the basis of the protrusion angle θ thus computed, and transmits the produced angle control signal to the protrusion angle control mechanism 17. Then, as shown in FIG. 8, the protrusion angle control mechanism 17 drives a control drive section on the basis of the angle control signal received. The driving of the control drive section causes the operating wire 22 to be pulled by the control drive section. As the operating wire 22 is pulled, the control piece 21 is turned about the pivot 24, against the biasing force of the biasing member 23. As a result, the angle of the control piece 21 is controlled.

In the case where the inclination angle of the contact surface 21a of the control piece 21 relative to the first direction X is smaller than the computed protrusion angle θ, the pulling force on the operating wire 22 is relaxed or released. As a result, the control piece 21 is turned about the pivot 24 in the direction opposite to the above-mentioned direction, by the biasing force of the biasing member 23. This increases the inclination angle of the contact surface 21a of the control piece 21 relative to the first direction X.

The description above describes an example in which the distance D from the outer wall of the side surface portion of the main body section 11 to the central portion of the bioptic target part M1 is computed. But the method is not limited in this regard.

For example, as shown in FIG. 6, the control unit 81 may measure a lower-limit distance D1 along the second direction Y from the outer wall of the side surface portion of the main body section 11 to a lower limit position permitting biopsy of the bioptic target part M1, and an upper-limit distance D2 along the second direction Y from the outer wall of the side surface portion of the main body section 11 to an upper limit position permitting biopsy of the bioptic target part M1. Then, a protrusion angle range θ1 to θ2 may be computed from the thus measured lower-limit distance D1 and upper-limit distance D2 and the distance L. Where a range is thus allowed for the protrusion angle θ, the accuracy in angle control by the protrusion angle control mechanism 17 can be set relatively low.

Next, the guide wire 3 is inserted into the insertion port 14 of the ultrasonic probe 2. In inserting the ultrasonic probe 2 into the bronchus N1 and the guide sheath 6, the guide wire 3 may be in the state of being inserted and passed in the insertion hole of the ultrasonic probe 2. That is, the guide wire can be positioned in and extend along the insertion hole in the ultrasonic probe 2 at the time the ultrasonic probe 2 is inserted or introduced into the bronchus N1.

As shown in FIG. 8, the guide wire 3 is bent by virtue of the guide wire 3 contacting the contact surface 21a of the control piece 21, whereby its advancing direction is controlled. Therefore, a distal portion of the guide wire 3 protrudes from the protrusion port 15 at the protrusion angle θ. Here, the protrusion angle θ of the guide wire 3 is so set that the guide wire 3 reaches the bioptic target part M1 in an assured and reliable manner. Accordingly, when the guide wire 3 is inserted further into the bronchus N1, the distal portion of the guide wire 3 reaches or is able to accurately puncture the bioptic target part M1.

Figure 9:
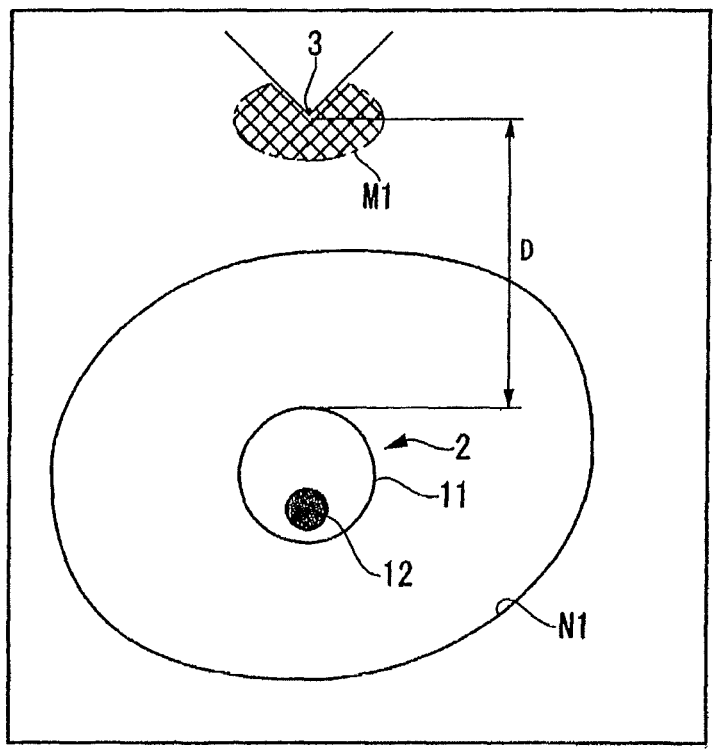
FIG. 9 is an illustration of an example of an in vivo tomographic image displayed on the image diagnosis unit in the first embodiment of the biopsy system disclosed here, where the tomographic image shows the condition where the guide wire is penetrating the bioptic target part.

FIG. 9 illustrates an example of the tomographic image displayed on the image display unit 82 of the image diagnosis unit 7, in the condition where the bioptic target part M1 is punctured by the guide wire 3.

In this instance, the guide wire 3 is displayed on the image display unit 82 of the image diagnosis unit 7 together with a cross-sectional image of the main body section 11 and a tomographic image of the inside of the bronchus N1, as for example shown in FIG. 9. Thus, the position of the guide wire 3 can be checked on the ultrasonic image. Therefore, any error in the protrusion position of the guide wire 3 can be rather easily corrected, so that the guide wire 3 can puncture the bioptic target part M1 in a reliable manner. Consequently, the position of the bioptic target part M1 can be marked by the guide wire 3.

In addition, the guide wire 3 is formed to be extremely thin, as compared with the biopsy device 4. Therefore, the ultrasonic probe 2 and the guide wire 3 can be inserted into the vicinity of alveoli N2 (see FIG. 5) present in the periphery of the bronchus N1.

Figure 10:
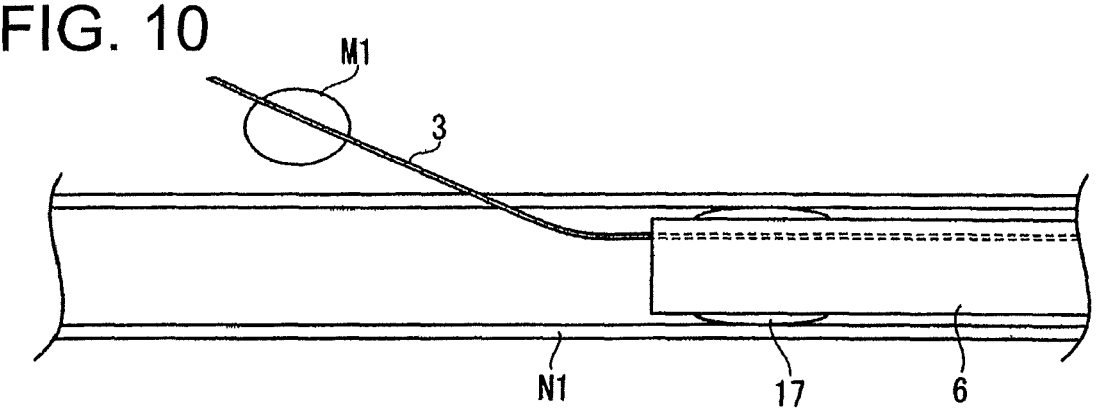
FIG. 10 illustrates a state in use of the first embodiment of the biopsy system showing the condition where the tomographic image pick-up device is pulled out of a sheath.
Figure 11:
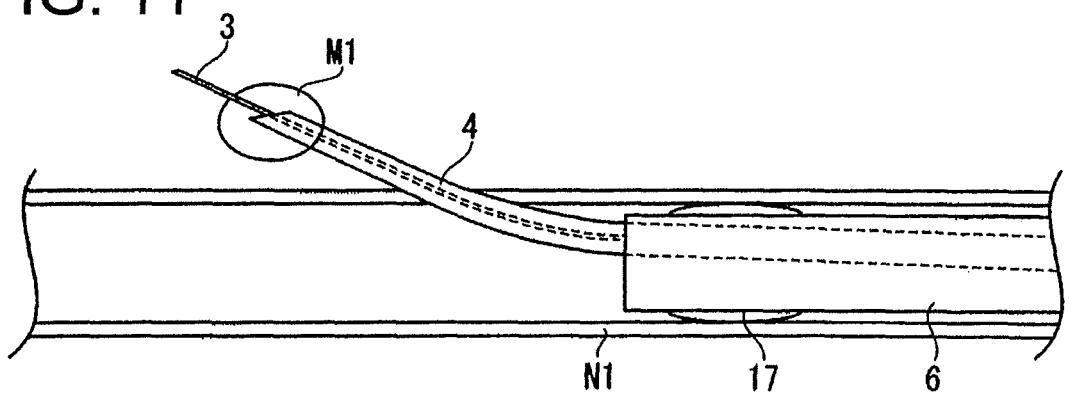
FIG. 11 illustrates a state in use of the first embodiment of the biopsy system, showing the condition where the biopsy device has been inserted to the bioptic target part.

FIG. 10 is an illustration of a state in which the ultrasonic probe 2 is pulled out of the guide sheath 6, and FIG. 11 is an illustration of a state in which the biopsy device 4 is inserted into the bioptic target part M1.

Subsequently, as shown in FIG. 10, in the condition where the bioptic target part M1 is punctured by the guide wire 3, the ultrasonic probe 2 is pulled out of the guide sheath 6 and out of the bronchus N1 (living body) along the guide wire 3. Even after the ultrasonic probe 2 is thus withdrawn, the guide wire 3 remains inside the bronchus N1 while puncturing the bioptic target part M1. Consequently, the position of the bioptic target part M1 can be grasped, without using X-rays or CT.

Next, as shown in FIG. 4, a proximal portion of the guide wire 3 is inserted into the ring section 16 at the distal end portion of the biopsy device 4. Then, as shown in FIG. 11, the biopsy device 4 is advanced in the guide sheath 6 toward the bronchus N1 along the guide wire 3. Since the guide wire 3 is penetrating the bioptic target part M1, the biopsy device 4 can be made to reach the bioptic target part M1 assuredly.

Subsequently, the bioptic target part M1 is scraped and sampled by a distal portion of the biopsy device 4. Then, the suction device 9 is driven to suck the tissue of the bioptic target part M1 that is sampled by the distal portion of the biopsy device 4. When the sampling of the tissue is completed, the biopsy device 4 is withdrawn out of the bronchus N1 along the guide wire 3. As a result, the biopsy based on the use of the biopsy system 1 according to this embodiment is completed.

This example of the biopsy method uses the suction device 9, but it is also possible to carry out a biopsy method which does not utilize the suction device 9. Thus, the biopsy method need not include use of suction or a suction device.

As a general summary, the biopsy method using the biopsy system 1 according to this embodiment includes the following aspects.

(1) inserting the ultrasonic probe 2 into a living body and acquiring an ultrasonic image;
(2) puncturing a bioptic target part M1 with the guide wire 3 while observing the ultrasonic image acquired by the inserted ultrasonic probe 2;
(3) withdrawing the ultrasonic probe 2 out of the living body after the puncturing with the guide wire 3;
(4) inserting the biopsy device 4 along the guide wire 3 to the bioptic target part M1 in the living body after the withdrawal of the ultrasonic probe 2 out of the living body; and
(5) sampling tissue of the bioptic target part M1 with the inserted biopsy device 4.

In this embodiment, at the time of inserting the biopsy device 4, only the biopsy device 4 is inserted into the living body, instead of inserting the biopsy device 4 into the living body together with other devices such as the ultrasonic probe 2. In addition, the guide wire 3 for guiding the biopsy device 4 is configured to be extremely thin and so it is not necessary to take the thickness of the guide wire 3 into account in setting the thickness of the biopsy device 4.

This makes it possible to set the thickness of the biopsy device 4 without being limited by the size (thickness) of other devices, and to form the biopsy device 4 at such a thickness level that it can be inserted into the periphery of a bronchus Consequently, the amount of tissue which can be sampled by the biopsy device 4 can be increased, and more accurate diagnosis can be carried out.

Furthermore, the ultrasonic probe 2 can be inserted to the periphery of the bronchus N1, and the guide wire 3 and the bioptic target part M1 at a position spaced from the bronchus N1 can be checked on the ultrasonic image. Consequently, even a bioptic target part M1 which is at a position spaced from the bronchus N1, in the periphery of the bronchus N1 or in the vicinity of the alveoli N2, and which could not be reliably subjected to biopsy using other known techniques, can be relatively assuredly punctured with the guide wire 3.

Thus, by guiding the biopsy device 4 along the guide wire 3 to the bioptic target part M1, the tissue of the bioptic target part M1 formed in the periphery of the bronchus N1 at a position spaced from the bronchus N1 can be fairly assuredly sampled by the biopsy device 4.

In addition, while this example of the biopsy method involves inserting the ultrasonic probe 2 and the biopsy device 4 and the like into the bronchus N1 through the oral cavity P of the patient R, a different method can be utilized involving inserting the ultrasonic probe 2 and the biopsy device 4 into the bronchus N1 via a nasal cavity of the patient R.

Furthermore, even after the biopsy device 4 is withdrawn out of the bronchus N1, the guide wire 3 marking the bioptic target part M1 remains inside the bronchus N1 in the state of penetrating the bioptic target part M1. Therefore, even when the biopsy device 4 is again inserted, the biopsy device 4 can be made to reach the bioptic target part M1 initially subjected to biopsy. Consequently, a bioptic step can be repeated, as required, so that the tissue necessary for diagnosis can be sampled in a large amount.

A modification of the tomographic image pick-up device in the biopsy system will now be described below with reference to FIG. 12. The tomographic image pick-up device 201 according to this modification differs from the above-described ultrasonic probe 2 shown in FIG. 2 in the configuration of the protrusion angle control mechanism in the ultrasonic probe. The following describes this modified protrusion angle control mechanism. Features in this embodiment of the biopsy system which are the same as features in the embodiment described above are identified by common reference numerals, and a detailed discussion of such features is not repeated here.

Figure 12:
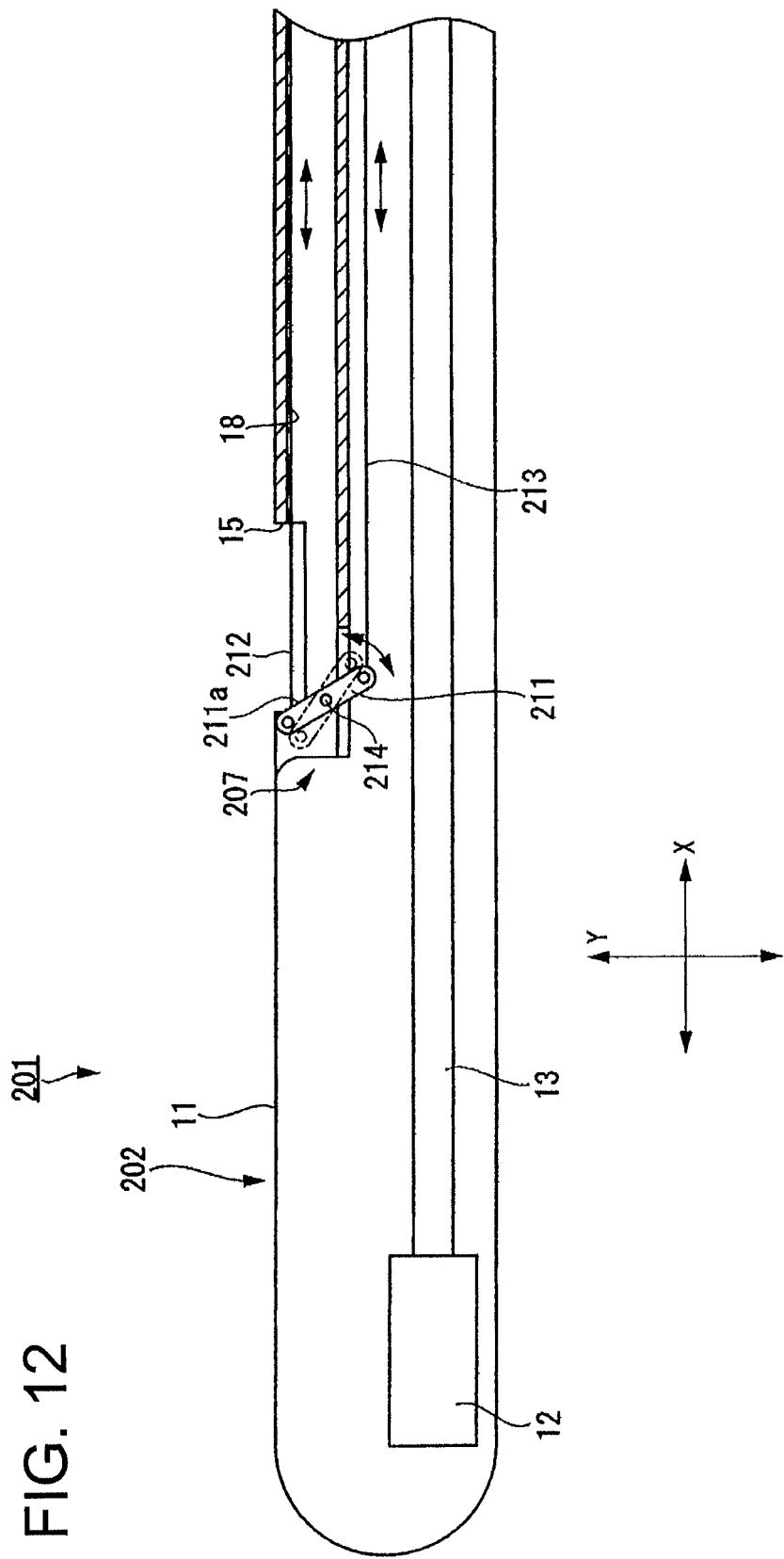
FIG. 12 is a cross-sectional view showing a modification of the tomographic image pick-up device in the biopsy system.
Figure 13A:
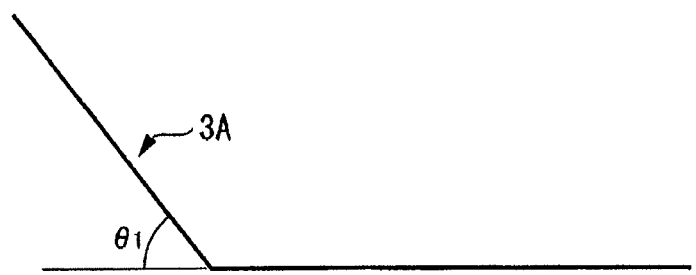
FIGS. 13A to 13F are plan views respectively of a plurality of the guide wires with different bend angles in the first embodiment of the biopsy system disclosed here.
Figure 13B:
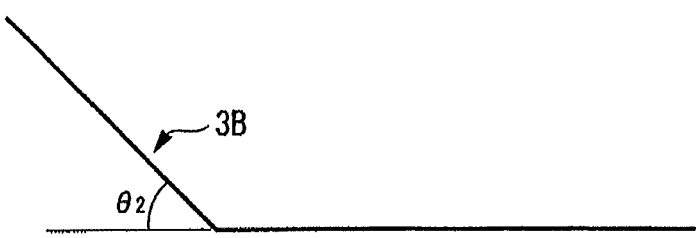
Figure 13C:
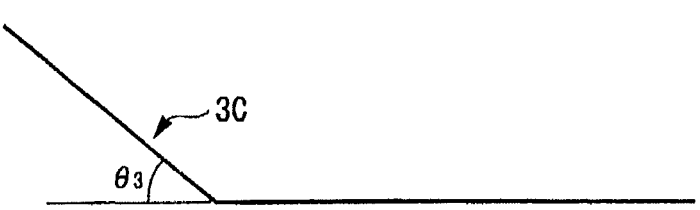
Figure 13D:
Figure 13E:
Figure 13F:

As shown in FIG. 12, an ultrasonic probe 202 constituting the tomographic image pick-up device 201 is provided with a protrusion angle control mechanism 207. The protrusion angle control mechanism 207 includes a control piece 211, a first operating wire 212, a second operating wire 213, a pivot 214, and a control drive section.

The control piece 211 is formed in a tongue-like shape (tongue-shaped), and is disposed at a protrusion port 15 on the distal end side of a main body section 11. The first operating wire 212 is attached to one end, on the protrusion port 15 side, of the control piece 211. The second operating wire 213 is attached to the other end, on the side opposite to the one end, of the control piece 211.

In addition, the pivot 214 is provided at an intermediate portion, between the one end and the other end, of the control piece 211. The control piece 211 is turnably supported on the main body section 11 through the pivot 214. The control piece 211 is turned along a plane defined by the first direction X and the second direction Y.

The first operating wire 212 and the second operating wire 213 are so arranged that they can be advanced and retracted (moved in the distal and proximal directions) along the first direction X in which the main body section 11 extends. End portions of the first operating wire 212 and the second operating wire 213 which are at opposite ends from the control piece 211 are connected to the control drive device.

When the first operating wire 212 is pulled while the second operating wire 213 is loosened (i.e., the second operating wire 213 is released or free to move), the control piece 211 is turned about the pivot 214. That is, the control piece 211 rotates in the clockwise direction. In this modification, the angle of a contact surface 211a of the control piece 211 relative to the first direction X is enlarged. In other words, the control piece 211 is turned in such a direction that the contact surface 211a approaches a state of being orthogonal to the first direction X.

On the other hand, when the second operating wire 213 is pulled whereas the first operating wire 212 is loosened (i.e., the first operating wire 212 is released or free to move), the control piece 211 is turned about the pivot 214 in a direction opposite to the above-mentioned direction. That is, the control piece 211 rotates in the counter-clockwise direction. In this modification, the angle of the contact surface 211a of the control piece 211 relative to the first direction X is reduced. In other words, the control piece 211 is turned in such a direction that the contact surface 211a approaches a state of being parallel to the first direction X.

The other aspects of the ultrasonic probe 2 are the same as those of the above-described ultrasonic probe 2 shown in FIG. 2m and so a detailed description of such features is not repeated. According to the ultrasonic probe 202 having the protrusion angle control mechanism 207 as described above, the same or similar operation, biopsy method and effect as those described above concerning the ultrasonic probe 2 shown in FIG. 2 can be obtained.

The setting of the protrusion angle θ of the guide wire 3 is not limited to the method of controlling the angle control mechanism in the ultrasonic probe 2 as described above. In this modification, the guide wire 3 is inserted into the proximal end side of the main body section 11 of the ultrasonic probe 2 via an insertion port 14. Therefore, the guide wire 3 can be replaced after the insertion of the ultrasonic probe 2 into a bronchus N1. Accordingly, the protrusion angle θ of the guide wire 3 can also be controlled by the method which will be described later.

FIGS. 13A to 13F show plan views of guide wires which differ in bend angle.

For example, as shown in FIGS. 13A to 13F, a plurality of guide wires 3A to 3F having distal portions preliminarily bent at respective bend angles θ1 to θ6 with respect to proximal portions are prepared. The bend angles θ1 to θ6 of the guide wires 3A to 3F are set to be different from one another (angle θ1>angle θ2>angle θ3>angle θ4>angle θ5>angle θ6). From among the plurality of guide wires 3A to 3F, the one that has an optimal bend angle is selected and put to use.

While an example in which the six guide wires 3A to 3F are prepared has been described in this embodiment, the number of guide wires to be prepared is not limited to this value.

According to the method in which a guide wire having an optimal bend angle is selected from a plurality of guide wires, time and effort in operating the ultrasonic probe 2 can be saved. In addition, the protrusion angle control mechanism 17 for controlling the protrusion angle of the guide wire 3, which mechanism has been provided for the ultrasonic probe 2, can be eliminated. This allows simplification of the configuration of the ultrasonic probe 2.

Figure 14:
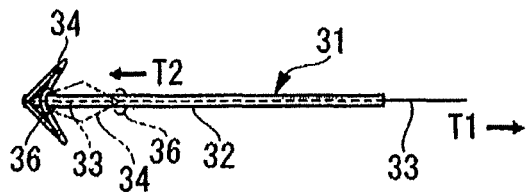
FIG. 14 is a plan view of a first modification of the guide wire used in the biopsy system disclosed here.
Figure 15:
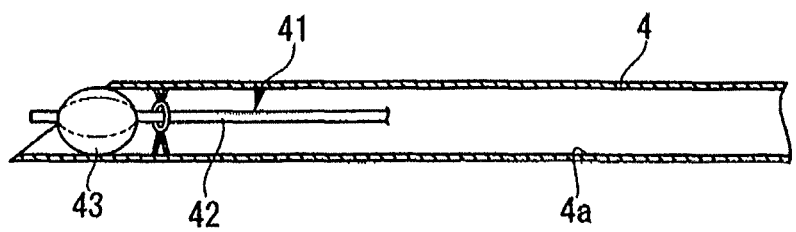
FIG. 15 is a plan view of a second modification of the guide wire used in the biopsy system disclosed here.

Now, modifications of the guide wire and the biopsy device will be described below with reference to FIGS. 14 to 18. FIG. 14 is a plan view of the guide wire showing a first modification of the guide wire, and FIG. 15 is a plan view of the guide wire showing a second modification of the guide wire.

The guide wire 31 according to the first modification shown in FIG. 14 includes a wire main body 32 having a distal portion configured to puncture a living body, a traction wire 33, and a slip-off preventive section 34. The slip-off preventive section 34 is configured to be bendable at its intermediate portion. One end of the slip-off preventive section 34 is fixed to the distal end of the wire main body 32, and the other end of the slip-off preventive section 34 is fixed to a sliding section 36. The sliding section 36 is roughly ring-like shape (ring-shaped), and is supported by (mounted on) the wire main body 32 so as to be slidable in the axial direction of the wire main body 32.

The traction wire 33 is positioned in and extends along the wire main body 32 so that the traction wire 33 can be advanced and retracted (moved in the distal and proximal directions) relative to the wire main body 32. A distal portion of the traction wire 33 is led out via the distal end of the wire main body 32 to the outside of the wire main body 32, and is fixed to the sliding section 36 which is slidably supported on the wire main body 32.

When the traction wire 33 is pulled toward the proximal end side in the axial direction, namely, in the direction of arrow T1 in FIG. 14, the sliding section 36 is slid in the direction of arrow T2 in FIG. 14, and moves toward the distal end side of the wire main body 32. Therefore, the slip-off preventive section 34 fixed to the sliding section 36 at the other end thereof is bent at its intermediate portion, to be spread in the radial outward direction of the wire main body 32.

When the guide wire 31 punctures a bioptic target part M1 (see FIG. 8), the slip-off preventive section 34 is erected in relation to the wire main body 32, whereby the slip-off preventive section 34 serves as a barb (anchor). This helps ensure that at the time of withdrawing the ultrasonic probe 2 (see FIG. 10) or at the time of inserting the biopsy device 4 (see FIG. 11) or in other similar situations, the guide wire 31 penetrating or puncturing a bioptic target part M1 can be prevented from being disengaged from the bioptic target part M1 or being positionally shifted. The slip-off preventive section 34 (barb/anchor) is configured so that the biopsy device 4 does not exceed the radially enlarged barb 34 in size. In other words, when the biopsy device 4 is pushed by distal side of guide wire 31, the slip-off preventive section 34 (radially enlarged barb/anchor) and the distal end of biopsy 4 abut one another.

A guide wire 41 according to the second modification shown in FIG. 15 includes a wire main body 42 having a distal portion configured to puncture a living body, and a balloon 43. The balloon 43 is fixed to a distal portion of the wire main body 42 so that it can be inflated and deflated. In using the guide wire 41 according to this second modification, the balloon 43 is inflated after tissue is sampled by the biopsy device 4 shown in FIG. 11. This results in that an opening on the distal side of the biopsy device 4 is closed by the inflated balloon 43.

In addition, in the condition where the distal-side opening of the biopsy device 4 is closed, the guide wire 41 is withdrawn out of a bronchus N1 together with the biopsy device 4. Therefore, at the time of pulling the biopsy device 4 out of the bronchus N1, the sampled tissue can be prevented from falling through the distal-side opening of the biopsy device 4. This makes it possible to inhibit or prevent metastasis (dissemination) of a lesion to another part due to the fallen tissue.

The balloon 43 serves as an anchor. This helps ensure that at the time of withdrawing the ultrasonic probe 2 (see FIG. 10) or at the time of inserting the biopsy device 4 (see FIG. 11) or in other similar situations, the guide wire 41 penetrating or puncturing the bioptic target part M1 can be prevented from being disengaged from the bioptic target part M1 or being positionally shifted. In other words, each of the guide wires 31 and 41 shown in FIGS. 14 and 15 is provided at its distal end with a slip-off preventive mechanism, or so-called anchoring mechanism. The balloon 43 in the inflated condition prevents slip-off involving two movements, when the ultrasonic probe 2 is pulled outside of the living body and when the biopsy device 4 is pushed toward the distal end of the guide wire 41. The inflated balloon 43 is held by or between tissue of the lung, because the guide wire 41 is in a punctured state in which the guide wire is punctured in the lung tissue.

Figure 16:
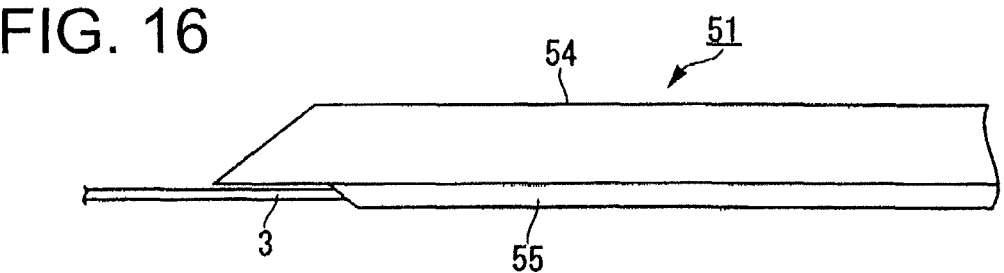
FIG. 16 is a plan view of a first modification of the biopsy device used in the biopsy system disclosed here.
Figure 17:
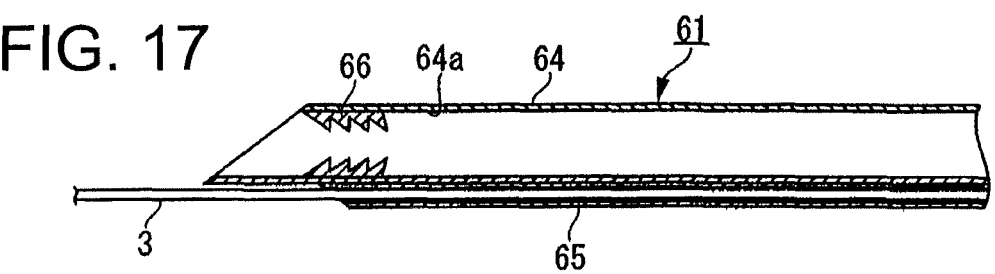
FIG. 17 is a cross-sectional view of a second modification of the biopsy device used in the biopsy system disclosed here.
Figure 18:
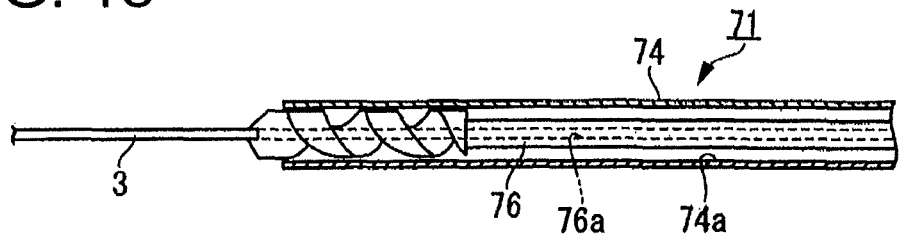
FIG. 18 is a cross-sectional view of a third modification of the biopsy device used in the biopsy system disclosed here.

FIG. 16 is a plan view showing a first modification of the biopsy device, FIG. 17 is a cross-sectional view showing a second modification of the biopsy device, and FIG. 18 is a cross-sectional view showing a third modification of the biopsy device.

As shown in FIG. 16, a biopsy device 51 according to the first modification includes a device main body 54, and a guide wire lumen 55. The device main body 54 is a hollow tubular shape open at both ends, like the biopsy device 4 according to the first embodiment. A distal portion of the device main body 54 is configured to puncture a living body, so that tissue of a living body can be sampled thereby.

The guide wire lumen 55 is fixed to a side surface portion of the device main body 54 and extends along the direction in which the device main body 54 extends. A guide wire 3 is positioned in and extends along the guide wire lumen 55. The biopsy device 51 is moved while being guided by the guide wire 3.

As shown in FIG. 17, a biopsy device 61 according to the second modification includes a device main body 64, and a guide wire lumen 65 in which a guide wire 3 is positioned, like the biopsy device 51 according to the first modification. The inner surface of the tube hole 64a on the distal end side of the device main body 64 is provided with a barb section 66.

The barb section 66 helps ensure that at the time of puncturing a bioptic target part M1 with the device main body 64 or at the time of withdrawing the device main body 64 out of a bronchus N1, sampled tissue can be prevented from falling out of the open distal end portion of the device main body 64. The tube hole 4a of the biopsy device 4 according to the first embodiment may also be provided with such a barb section 66.

As shown in FIG. 18, a biopsy device 71 according to the third modification includes a biopsy sheath 74, and a drill-like (drill-shaped) tissue sampling section 76 rotatably disposed in a tube hole 74a of the biopsy sheath 74. The tissue sampling section 76 is formed in a roughly cylindrical shape, and is provided with a spiral groove in an outer side surface portion. The tissue sampling section 76 is formed with a penetrating hole 76a penetrating the tissue sampling section 76 along the axial direction. A guide wire 3 is positioned in and extends along the penetrating hole 76a, The biopsy sheath 74 covers the tissue sampling section 76.

When a bioptic target part M1 is punctured, the tissue sampling section 76 of the biopsy device 71 is rotated about the guide wire 3. Then, tissue of the bioptic target part M1 is scraped off by the spiral groove formed in the tissue sampling section 76. As the tissue sampling section 76 is rotated, the tissue thus scraped is conveyed along the spiral groove, to be drawn into the tube hole 74a of the biopsy sheath 74.

While an example in which only the tissue sampling section 76 is rotated has been described in the biopsy device 71 according to this modification, a configuration may be adopted in which the tissue sampling section 76 is fixed inside the tube hole 74a of the biopsy sheath 74, and the biopsy sheath 74 is rotated together with the tissue sampling section 76. Furthermore, the guide wire 3 may also be rotated together with the biopsy device 71 when the biopsy device 71 is rotated.

The guide wires 31, 41 according to the first and second modifications described above and the biopsy devices 51 to 71 according to the first to third modifications may be used in combinations. The biopsy devices 51 to 71 according to the modifications described above are not restrictive; for example, biopsy forceps having a guide wire lumen may also be used.

A second embodiment of the biopsy system representing another example of the disclosure here, will now be described below with reference to FIG. 19.

The biopsy system 101 according to the second embodiment differs from the biopsy system 1 according to the first embodiment in the position of the insertion port provided in the main body section of the ultrasonic probe. Thus discussion which follows will focus primarily on the ultrasonic probe, and features that are the same or similar to those described above in the biopsy system 1 are denoted by common reference numerals, and a detailed descriptions of such features will not be repeated.

Figure 19:
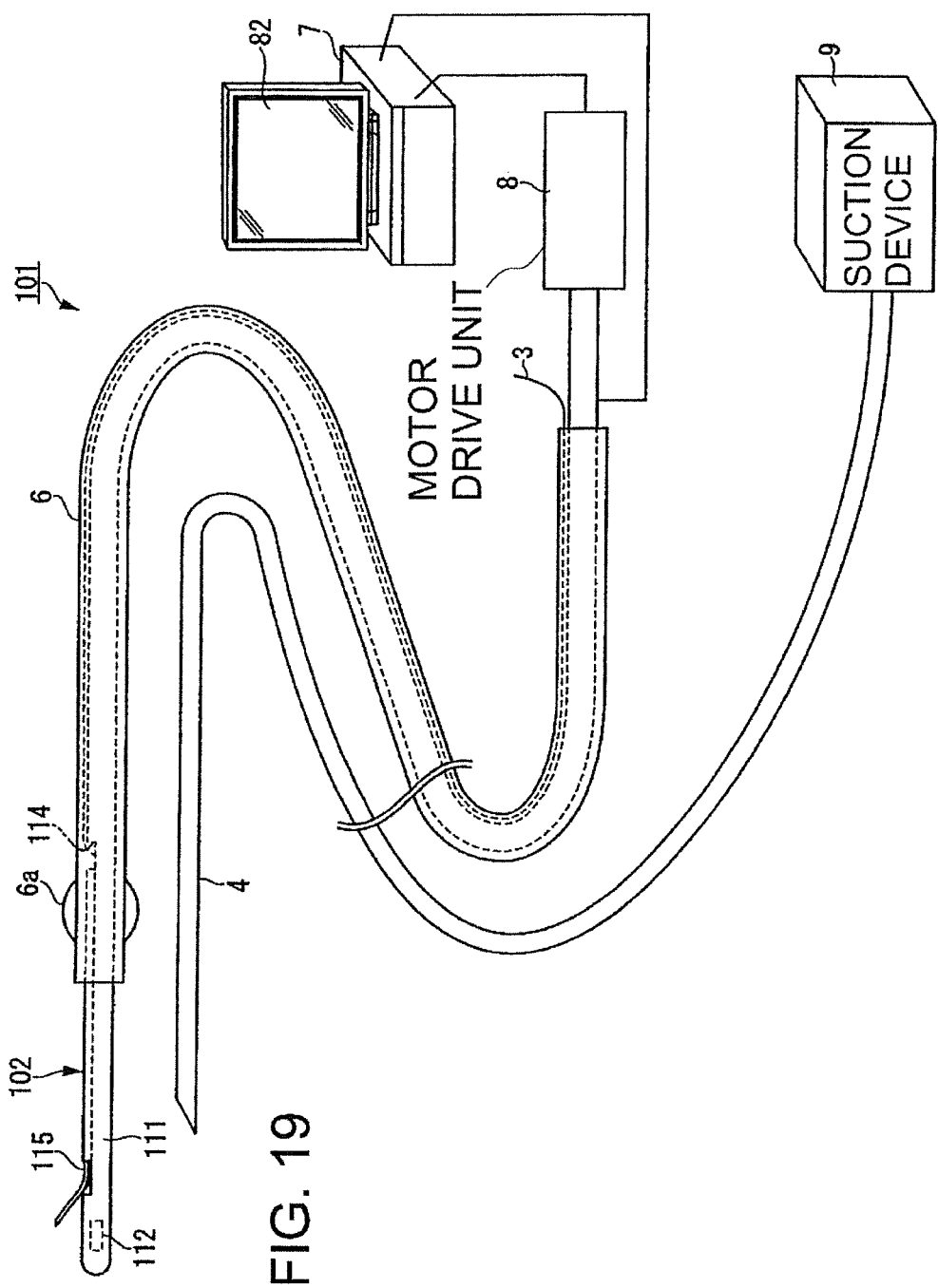
FIG. 19 is a schematic configuration view showing a second embodiment of the biopsy system.

As shown in FIG. 19, an ultrasonic probe 102 in the biopsy system 101 includes a main body section 111, and a sensor section 112 incorporated in the main body section 111. A distal portion of the main body section 111 is formed, in the vicinity of the sensor section 112, with a protrusion port 115 from which a guide wire 3 is protruded.

In addition, the main body section 111 is provided, in the vicinity of the protrusion port 115, with an insertion port 114 through which the guide wire 3 is inserted. The insertion port 114 is formed on the proximal end side, in the axial direction of the main body section 111, relative to the protrusion port 115. In other words, the insertion hole in the ultrasonic probe 102 (i.e., the hole in the ultrasonic probe in which the guide wire is positioned and along which the guide wire extends) according to the second embodiment is shorter than the insertion hole in the ultrasonic probe 2 according to the first embodiment. The guide wire 3 is inserted and passed in only a distal portion of the ultrasonic probe 102.

According to the biopsy system 101 in the second embodiment, the length of the insertion hole in which the guide wire 3 is positioned and extends is shortened. Therefore, an operation of withdrawing the ultrasonic probe 102 while leaving the guide wire 3 in situ can be facilitated. In addition, the length of the guide wire 3 in the biopsy system 101 according to the second embodiment can be reduced, as compared with the guide wire 3 in the biopsy system 1 according to the first embodiment.

In the biopsy system 101 according to the second embodiment, it is preferable to insert the guide wire 3 into the ultrasonic probe 102 and thereafter insert the ultrasonic probe 102 into a bronchus (living body) N1. The control of the protrusion angle θ of the guide wire 3 is preferably conducted not by a method in which a guide wire is selected from a plurality of guide wires each angled at a specified angle such as shown in FIGS. 13A-13F, but by a method in which the protrusion angle θ is controlled by the protrusion port 115 of the ultrasonic probe 102.

The other aspects and features of the biopsy system according to this second embodiment are the same as those in the biopsy system 1 according to the first embodiment described above, so a detailed description of such aspects and features is not repeated. According to the biopsy system 101 having the ultrasonic probe 102 as above-described, also, the same or similar operation and effect to those of the biopsy system 1 according to the first embodiment described above can be obtained.

Now, another modification of the tomographic image pick-up device will be described below with reference to FIGS. 20A and 20B which are cross-sectional views of a tomographic image pick-up device.

This tomographic image pick-up device 301 differs from the tomographic image pick-up device 1 according to the first embodiment in that a sensor section is attachable to and detachable from a main body section of an ultrasonic probe. The main body section and the sensor section of the ultrasonic probe of this embodiment will be described below. Features and aspects of that are the same as features and aspects in earlier described embodiments are identified by common reference numerals, and a detailed discussion of such features and aspects is not repeated here.

Figure 20A:
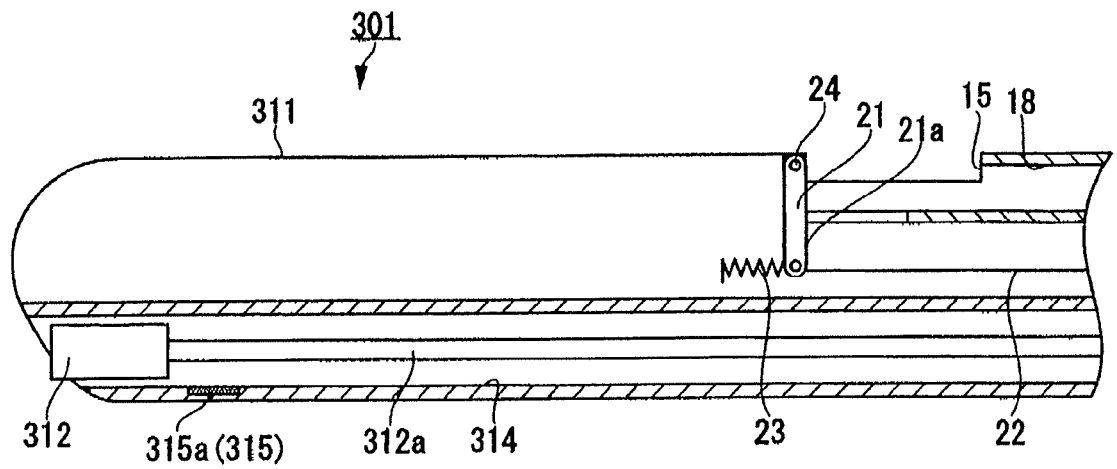
Figure 20B:
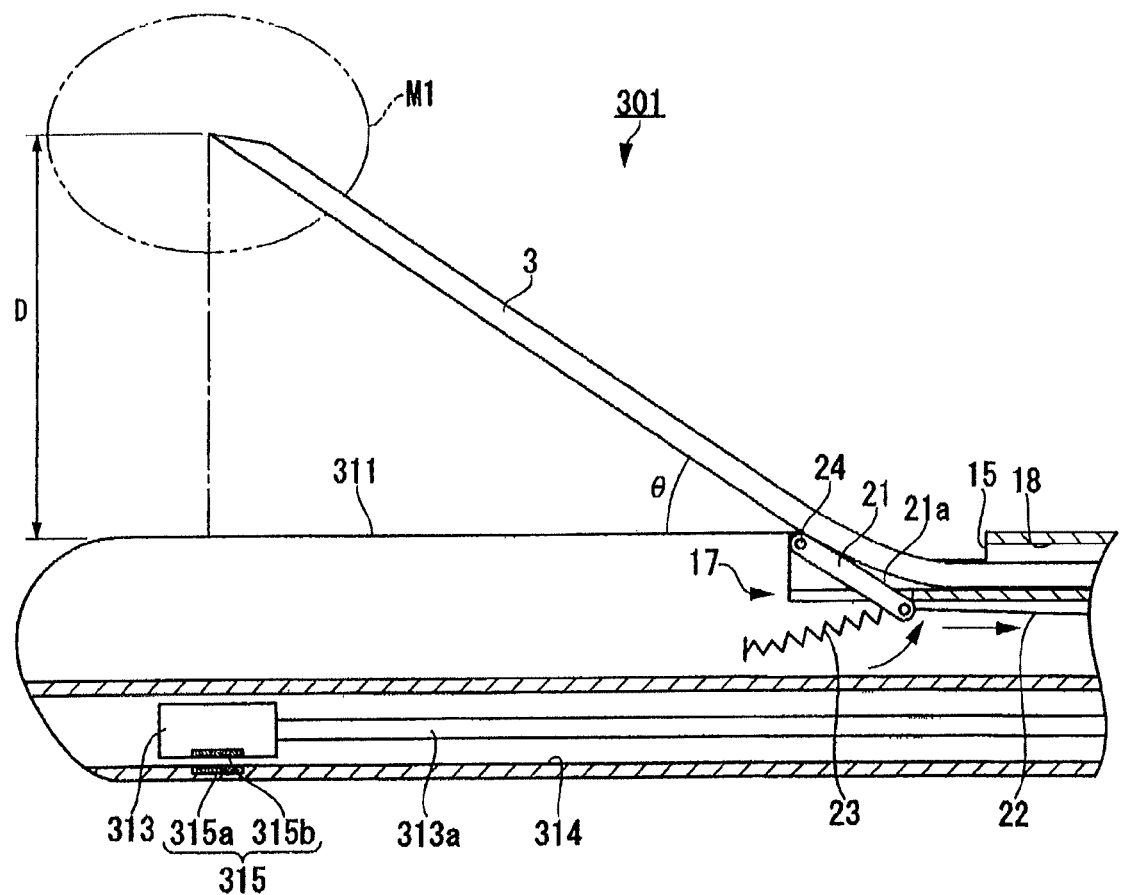

As shown in FIGS. 20A and 20B, the main body section 311 of the tomographic image pick-up device 301 is provided with a protrusion angle control mechanism 17, and includes an insertion hole 18 in which a treating instrument 3 (e.g., guide wire, biopsy device) is located and through which the treating instrument 3 extends, and an insertion hole 314 in which a first sensor section 312 and a second sensor section 313 are detachably inserted. The insertion hole 314 penetrates or extends through the main body section 311 along the axial direction of the main body section 311. At the distal end in the axial direction of the main body section 311, an opening of the insertion hole 314 is located.

As shown in FIG. 20A, the first sensor section 312 is a sensor which is composed, for example, of a camera and which permits visual checking of the axially forward side of the main body section 311. The first sensor section 312 is attached to the distal end in the axial direction of a bendable insertion member 312a.

As shown in FIG. 20B, the second sensor section 313 includes an ultrasonic transducer which transmits an ultrasonic wave to a living body, and a reception element which receives an ultrasonic wave signal reflected from the living body. The second sensor section 313 makes it possible to acquire a tomographic image of the inside of a living body as an ultrasonic image. In addition, the second sensor section 313 is attached to the distal end in the axial direction of a bendable insertion member 313a, like the first sensor section 312.

Furthermore, the main body section 311 and the second sensor section 313 are provided with a fixing mechanism 315 by which the second sensor section 313 is fixed at a predetermined position in the insertion hole 314. The fixing mechanism 315 includes a main body-side magnet 315a provided in the insertion hole 314 in the main body section 311 (e.g., embedded in the wall of the main body section 311 and facing toward the insertion hole 314), and a sensor-side magnet 315b provided in the second sensor section 313. The main body-side magnet 315a and the sensor-side magnet 315b attract each other by their magnetic forces, whereby the second sensor section 313 is attracted to and fixed at the predetermined position in the insertion hole 314.

While an example has been described in which the fixing mechanism 315 is in the form of magnets in the main body section 311 and the second sensor section 313, the biopsy system is not limited in this regard. For instance, a configuration may be adopted in which at least one of the main body section 311 and the second sensor section 313 is provided with a magnet, whereas the other of the main body section 311 and the second sensor section 313 is provided with a ferromagnetic body formed from iron or the like.

An example of operation of the tomographic image pick-up device 301 will now be described. Referring initially to FIG. 20A, the first sensor section 312 as a sensor permitting visual checking of the forward side is inserted into the insertion hole 314 in the main body section 311. Next, using image information sent or acquired from the first sensor section 312, the main body section 311 is guided to a target part in a living body.

After the main body section 311 has reached the target part in the living body, the first sensor section 312 is pulled out of the insertion hole 314. Subsequently, the second sensor section 313 for acquiring a tomographic image of the inside of the living body is inserted into the insertion hole. Then, the main body-side magnet 315a and the sensor-side magnet 315b are fixed to each other by mutual attraction. Consequently, the second sensor section 313 can be fixed at a predetermined position in the insertion hole 314.

The other configurations are the same as those in the tomographic image pick-up device 1 according to the first embodiment described above, and so a detailed description of such features is not repeated. According to the tomographic image pick-up device 301 having the main body section 311 as above-described, also, the same or similar operation and effect to those of the tomographic image pick-up device 1 according to the above-described first embodiment can be obtained.

In addition, the insertion hole 314 in which to insert the first sensor section 312 and the second sensor section 313 may be used as an insertion hole in which a guide wire 3 is to be inserted and passed. Specifically, at the time of re-inserting the main body section 311 into the living body after the guide wire 3 is set indwelling in a target part, the main body section 311 may be inserted along the guide wire 3. Then, after the main body section 311 has reached the target part, the guide wire 3 may be withdrawn out of the insertion hole 314, and the second sensor section 313 inserted into the insertion hole 314. This embodiment may thus involve the use of multiple guide wires.

Now, a modification of the fixing mechanism of the tomographic image pick-up device 301 will be described below with reference to FIGS. 21A and 21B. The fixing mechanism will be described below, and features and aspects of the tomographic image pick-up device that are the same as features and aspects described above ware identified by common reference numerals and a detailed description of such features and aspects is not repeated.

Figure 21A:
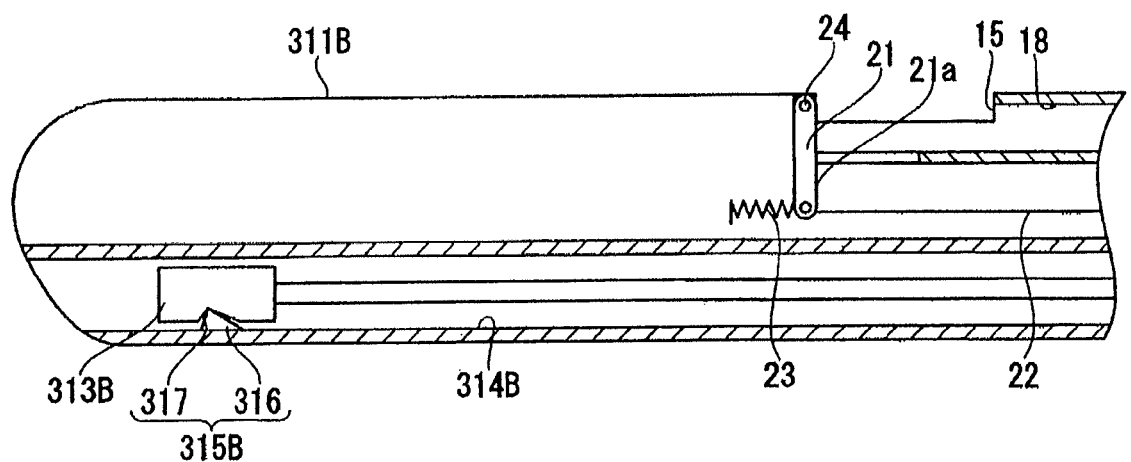
Figure 21B:
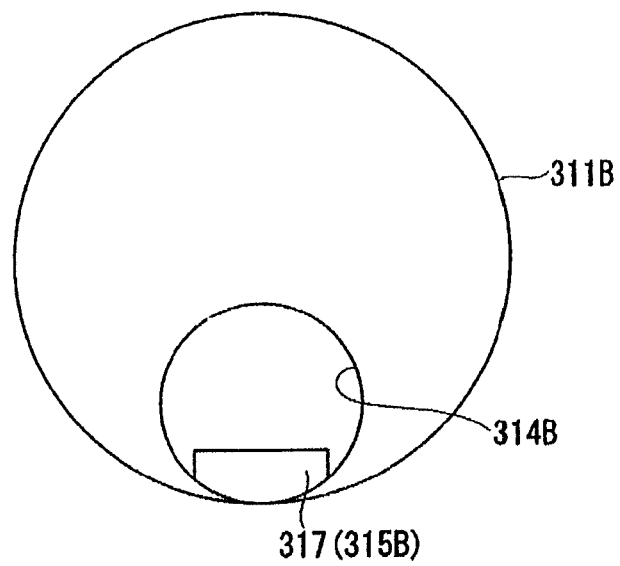

As shown in FIGS. 21A and 21B, a fixing mechanism 315B includes an engaging projection 316 projecting inwardly from the inner wall surface surrounding the insertion hole 314B in the main body section 311B, and an engaging groove 317 in the second sensor section 313B. The engaging projection 316 projects from the wall surface of the insertion hole 314B in a radially inward direction. Engagement of the engaging projection 316 and the engaging groove 317 with each other fixes the second sensor section 313B at a predetermined position in the insertion hole 314B.

A first sensor section, in this modification, is not provided with an engaging groove 317. Therefore, the first sensor section is not fixed at that position in the insertion hole 314B at which the engaging projection 316 is provided. However, a configuration may be adopted in which the first sensor section is provided with the engaging groove 317 so that the first sensor section is also fixed at the same position as the fixing position for the second sensor section 313B.

In addition, when the first sensor section is inserted into the axially distal side in the insertion hole 314B relative to the second sensor section 313B (i.e., when the first sensor section and the second sensor section 313B are both located in the insertion hole 314B, with the first sensor section positioned distally of the second sensor section 313B), the diameter of the first sensor section may be set sufficiently smaller than the diameter of the second sensor section 313B so that the first sensor section will not interfere with the engaging projection 316.

While an example in which the second sensor section 313, 313B is fixed directly to the insertion hole 314, 314B has been described in this modification, this is not restrictive. For example, a configuration may be adopted in which a tubular member for accommodating the second sensor section in its tube hole is provided and the tubular member is provided with a fixing mechanism. Further, a configuration may be adopted in which the second sensor section can be supported in the tube hole of the tubular member so as to be rotatable about the axis thereof.

The present disclosure is not restricted to the embodiments described above and illustrated in the drawings, and various alterations are possible within the scope of the disclosure as defined in the claims. The biopsy system disclosed here is applicable not only to biopsy of bronchus but also to biopsy of other living body parts, for example, digestive organs such as small intestine, large intestine, esophagus, etc. or urinary organs such as urethra, etc.

The detailed description above describes features and aspects of embodiments of a biopsy system and method. The invention is not limited, however, to the precise embodiments and variations described and illustrated. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A biopsy system for performing biopsy of a bioptic target part in a living body comprising:
    an ultrasonic probe positionable in and removable from the living body and comprised of a main body section and a sensor section configured to transmit signals which are reflected off the bioptic target part in the living body and receive the reflected signals to produce a tomographic image of the bioptic target part;
    a guide wire possessing a distal end configured to puncture the bioptic target part so that the guide wire is in a punctured state;
    the main body section of the ultrasonic probe including a guide wire insertion hole having open opposite ends for receiving the guide wire, the ultrasonic probe being movable along the guide wire when the guide wire is positioned in the guide wire insertion hole, the main body possessing a longitudinal axis, and one of the open opposite ends of the guide wire insertion hole being a distal end;
    a biopsy device movable along the guide wire while the guide wire is in the punctured state and after the ultrasonic probe is removed from the living body to guide movement of the biopsy device to the bioptic target part, the biopsy device being configured to contact the bioptic target part and obtain a tissue sample of the bioptic target part for biopsy;
    an adjustable control piece which is adjustable to vary an angle of inclination of the control piece relative to the longitudinal axis of the main body section, the adjustable control piece being positioned at a protrusion port connecting with the distal end of the guide wire insertion hole so that the guide wire positioned in the guide wire insertion hole and moved in a distal direction contacts the control piece to control an angle of inclination at which the guide wire protrudes from the guide wire protrusion port;
    a control unit connected to the adjustable control piece to adjust the control piece; and wherein the control unit measures a lower-limit distance from a part of the probe to a lower limit position of the bioptic target part and an upper-limit distance from the part of the probe to an upper limit position of the bioptic target part, based on the tomographic image of the bioptic target part produced by the probe, and adjusts the control piece to an angle calculated based on the lower-limit distance, the upper-limit distance, and a distance from the sensor section to the protrusion port.

2. The biopsy system according to claim 1, further comprising a guide sheath in which is positionable the biopsy device and the ultrasonic probe.

3. The biopsy system according to claim 1, wherein the sensor section is rotatably positioned in the main body section.

4. The biopsy system according to claim 1, wherein the distal end of the guide wire comprises at least one of a tapered-off shape and a sharpened tip, so that the distal end of the guide wire is configured to puncture the bioptic target part in the living body.

5. A biopsy method comprising:
   inserting a probe into a living body, a bioptic target part being in the living body, the probe including a sensor section configured to emit signals which are reflected off the bioptic target part in the living body and to receive the signals reflected off the bioptic target part to obtain location information about a location of the bioptic target part in the living body;
   positioning a guide wire in an insertion hole of the probe, the insertion hole possessing a distal end, the guide wire protruding from a protrusion port which communicates with the distal end of the insertion hole;
   controlling an angle of protrusion at which the guide wire protrudes from the protrusion port by operating an angle control mechanism at the protrusion port based on the location information;
   puncturing the bioptic target part in the living body with the guide wire using the location information obtained from the signals reflected from the bioptic target part and received by the probe;
   withdrawing the probe while the bioptic target part remains punctured by the guide wire;
   inserting a biopsy device along the guide wire and guiding movement of the biopsy device by moving the biopsy device along the guide wire while the bioptic target part remains punctured by the guide wire;
   sampling tissue of the bioptic target part through use of the biopsy device;
   wherein the location information includes a lower-limit distance from a part of the probe to a lower limit position of the bioptic target part and an upper-limit distance from the part of the probe to an upper limit position of the bioptic target part; and
   adjusting a direction of the distal part of the guide wire to an angle calculated based on the lower-limit distance, the upper-limit distance, and a distance from the sensor section positioned in the probe to the protrusion port.

6. The biopsy method according to claim 5, wherein the probe is inserted into the living body while supported by a guide sheath, and the biopsy device is inserted into the living body while supported by the guide sheath.

7. The biopsy method according to claim 5, wherein the guide wire is one of a plurality of guide wires, each of the guide wires possessing a bend so that proximal and distal portions of each respective guide wire are oriented at a bend angle other than zero degrees, the method further comprising selecting one of the guide wires possessing an optimal bend angle based on the tomographic image.

* * * * *